(12) United States Patent
Kim et al.

(10) Patent No.: US 8,163,889 B2
(45) Date of Patent: Apr. 24, 2012

(54) PHYSIOLOGICALLY ACTIVE POLYPEPTIDE CONJUGATE HAVING PROLONGED IN VIVO HALF-LIFE

(75) Inventors: Young-Min Kim, Yongin-si (KR); Dae-Jin Kim, Seoul (KR); Sung-Min Bae, Seoul (KR); Chang-Ki Lim, Seongnam-si (KR); Se-Chang Kwon, Seoul (KR); Gwan-Sun Lee, Seoul (KR)

(73) Assignee: Hanmi Holdings Co., Ltd., Seoul (KR)

( * ) Notice: Subject to any disclaimer, the term of this patent is extended or adjusted under 35 U.S.C. 154(b) by 0 days.

(21) Appl. No.: 12/603,757

(22) Filed: Oct. 22, 2009

(65) Prior Publication Data

US 2010/0105869 A1 Apr. 29, 2010

Related U.S. Application Data

(63) Continuation of application No. 10/807,732, filed on Mar. 24, 2004, now abandoned, which is a continuation-in-part of application No. 10/659,195, filed on Sep. 9, 2003, now abandoned.

(30) Foreign Application Priority Data

| Mar. 13, 2003 | (KR) | 2003-0015744 |
|---|---|---|
| Jun. 5, 2003 | (KR) | 2003-0036408 |

(51) Int. Cl.
*C07K 16/00* (2006.01)

(52) U.S. Cl. .................................. 530/391.9

(58) Field of Classification Search ............ None
See application file for complete search history.

(56) References Cited

U.S. PATENT DOCUMENTS

| 4,232,119 A | 11/1980 | Carlsson et al. |
|---|---|---|
| 4,487,325 A | 12/1984 | Willingham |
| 5,045,312 A | 9/1991 | Aston et al. |
| 5,216,130 A | 6/1993 | Line et al. |
| 5,492,821 A | 2/1996 | Callstrom et al. |
| 5,601,825 A | 2/1997 | Hansen et al. |
| 6,340,742 B1 | 1/2002 | Burg et al. |
| 6,475,983 B1 | 11/2002 | Eid et al. |
| 2001/0028881 A1 | 10/2001 | Roffler et al. |
| 2002/0081664 A1 | 6/2002 | Le et al. |
| 2003/0211078 A1 | 11/2003 | Heavner |
| 2004/0115165 A1 | 6/2004 | Rosen et al. |
| 2006/0153839 A1 | 7/2006 | Mohamed et al. |

FOREIGN PATENT DOCUMENTS

| EP | 0622082 A1 | 11/1994 |
|---|---|---|
| WO | 9216221 | 10/1992 |
| WO | 97/24440 A1 | 7/1997 |
| WO | 01/03737 A1 | 1/2001 |
| WO | 01/23430 A3 | 4/2001 |
| WO | 03049684 A2 | 6/2003 |

OTHER PUBLICATIONS

Chaffee, S., et al., "IgG Antibody Response to Polyethylene Glycol-modified Adenosine Deaminase in Patients with Adenosine Deaminase Deficiency," J. Clin. Invest., vol. 89, pp. 1643-1651, 1992.
Zanme, A., et al., "Conjugates of Superoxide Dismutase with the Fc Fragment of Immunoglobulin G," J. Biochem., 110, 868-872 (1991).
Kita, Y., et al., "Characterization of a Polyethylene Glycol Conjugate of Recombinant Human Interferon-γ," Drug Design and Delivery, vol. 6, 157-167, 1990.
Savva, M., et al., "A genetically modified recombinant tumor necrosis factor-α conjugated to the distal terminals of liposomal surface grafted polyethyleneglycol chains," Int'l J. Pharmaceutics, 184, 45-51, 1999.
Paige, A.G., et al., "Prolonged Circulation of Recombinant Human Granulocyte-Colony Stimulating Factor by Covalent Linkage to Albumin Through a Heterobifunctional Polyethylene Glycol," Phar. Research., 12:12, 1883-1888, 1995.

*Primary Examiner* — Marianne P Allen
(74) *Attorney, Agent, or Firm* — Sughrue Mion, PLLC

(57) ABSTRACT

A protein conjugate having a prolonged in vivo half-life of a physiological activity, comprising i) a physiologically active polypeptide, ii) a non-peptidic polymer, and iii) an immunoglobulin, is useful for the development of a polypeptide drug due to the enhanced in vivo stability and prolonged half-life in blood, while reducing the possibility of inducing an immune response.

17 Claims, 16 Drawing Sheets

PHYSIOLOGICALLY ACTIVE POLYPEPTIDE CONJUGATE HAVING PROLONGED IN VIVO HALF-LIFE

CROSS REFERENCE TO RELATED APPLICATION

This is a continuation application of U.S. Ser. No. 10/807,732 filed Mar. 24, 2004, which is a continuation-in-part of U.S. Ser. No. 10/659,195, filed on Sep. 9, 2003, now abandoned, which claims priority from Korean patent application 2003-0036408, filed on Jun. 5, 2003 and from Korean patent application 200-0015744, filed on Mar. 13, 2003, the contents of which are incorporated herein by reference in their entirety.

FIELD OF THE INVENTION

The present invention relates to a long acting protein having a prolonged in vivo half-life and a preparation method thereof.

BACKGROUND OF THE INVENTION

Polypeptides are susceptible to denaturation or enzymatic degradation in the blood, liver or kidney. Because of the low stability of polypeptides, it has been required to administer a polypeptide drugs in a sustained frequency to a subject in order to maintain an effective plasma concentration of the active substance. Moreover, since polypeptide drugs are usually administrated by infusion, frequent injection of polypeptide drugs causes considerable discomfort to a subject. Thus, there have been many studies to develop a polypeptide drug which has an increased circulating half-life in the blood, while maintaining a high pharmacological efficacy thereof. Such desirous polypeptide drugs should also meet the requirements of enhanced serum stability, high activity, applicability to various polypeptides and a low probability of inducing an undesired immune response when injected into a subject.

One of the most widely used methods for improving the stability of proteins is the chemical modification of a polypeptide with highly soluble macromolecules such as polyethylene glycol ("PEG") which prevents the polypeptides from contacting with proteases. It is also well known that, when linked to a polypeptide drugs specifically or non-specifically, PEG increases the solubility of the polypeptide drug and prevents the hydrolysis thereof, thereby increasing the serum stability of the polypeptide drug without incurring any immune response due to its low antigenicity (Sada et al., *J. Fermentation Bioengineering*, 1991, 71: 137-139). However, such pegylated polypeptides have the disadvantages of lowering both the activity and production yield of an active substance as the molecular weight of PEG increases. An interferon conjugated with two activated PEGs as well as a PEG spacer which is linked to two polypeptides having different activities are disclosed in U.S. Pat. No. 5,738,846 and International Patent Publication No. WO92/16221, respectively; however, they do not show any distinctive effect in terms of prolonged activity of the physiologically active polypeptides in vivo.

It is also reported that the circulating half-life of a recombinant human granulocyte-colony stimulating factor ("G-CSF") can be prolonged by covalently linking it to albumin through a hetero-bifunctional PEG (Kinstler et al., *Pharmaceutical Research*, 1995, 12(12): 1883-1888). However, the stability of the modified G-CSF-PEG-albumin is merely 4 times higher than that of authentic G-CSF and, thus, it has not yet been put to practical use.

As another approach for enhancing the in vivo stability of physiologically active polypeptides, an active polypeptide fused with a stable protein is produced in a transformant by using recombinant technologies. For example, albumin is known as one of the most effective proteins for enhancing the stability of polypeptides fused thereto and there are many such fusion proteins reported (International Patent Publication Nos. WO93/15199 and 93/15200, and European Patent Publication No. 413,622). However, a fusion protein coupled with albumin still has the problem of reduced activity.

U.S. Pat. No. 5,045,312 discloses a method for conjugating growth hormone to bovine serum albumin or mouse immunoglobulin using a cross-linking agent such as carbodiimide, glutaraldehyde, acid chloride, etc. in order to enhance the activity of the growth hormone. However, this method is solely aimed at enhancing the activity of a target growth hormone. In addition, the use of chemical compounds such as carbodiimide, glutaraldehyde, acid chloride, etc. as a cross-linking agent is disadvantageous due to their potent toxicity and non-specificity of reaction.

It has been reported that immunoglobulins are capable of acting as antibodies to exhibit antibody-dependent cell cytotoxicity (ADCC) and complement dependent cytotoxicity (CDC), and sugar chains play an important role in the ADCC and CDC (Burton D., *Molec. Immun.* 22, 161-206, 1985). Notwithstanding the absence of sugar chains, an aglycosylated immunoglobulin has an blood half-life similar to that of the glycosylated one, however, its affinity to a complement or receptor decreases by 10 to 1000 folds to due to the deglycosylation (Waldmann H., *Eur. J. Immunol.* 23, 403-411, 1993; Morrison S., *J. Immunol.* 143, 2595-2601, 1989).

Although there have been many attempts to combine a physiologically active polypeptide with various macromolecules, all have failed to simultaneously increase the stability and the activity.

As an improved method for enhancing the stability of an active polypeptide and simultaneously maintaining the in vivo activity thereof, the present invention provides a protein conjugate comprising a physiologically active polypeptide, non-peptidic polymer and immunoglobulin, which are covalently interlinked to one another.

SUMMARY OF THE INVENTION

Accordingly, a primary object of the present invention is to provide a protein conjugate having a prolonged in vivo half-life of a physiologically active polypeptide without inducing an immune response in a subject, while minimizing the reduction in the polypeptide's activity.

Another object of the present invention is to provide a method for preparing a protein conjugate comprising a physiologically active polypeptide, a biocompatible non-peptidic polymer and an immunoglobulin, which are covalently interlinked.

A further object of the present invention is to provide a pharmaceutical composition comprising said physiologically active polypeptides having a prolonged in vivo half-life.

A still further object of the present invention is to provide a method for enhancing the in vivo stability and prolonging the circulating half-life of a physiologically active polypeptide, without sacrificing the activity thereof.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
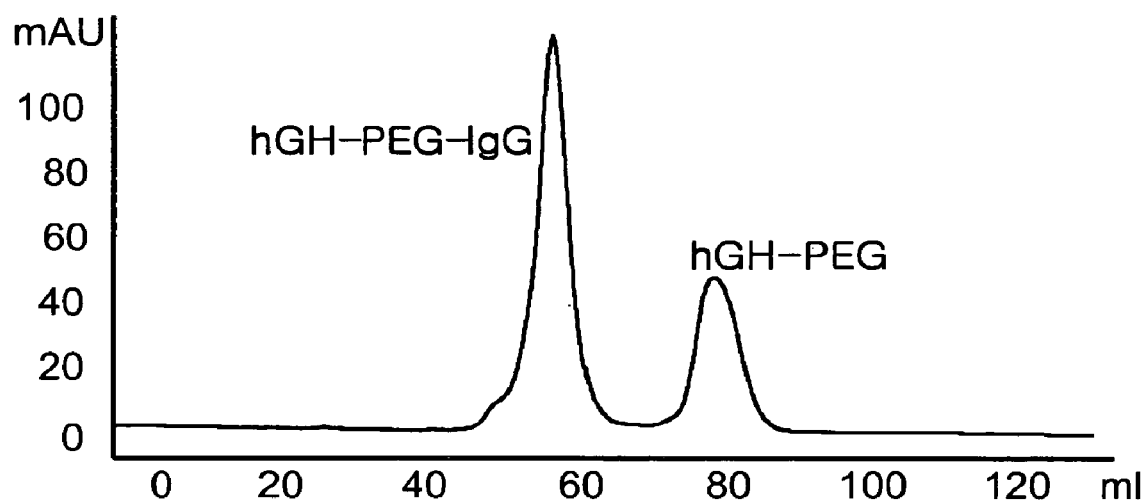
FIG. 1: a chromatogram of hGH-PEG-IgG conjugates.

The term "physiologically active polypeptide" as used herein refers to any polypeptide or protein having a useful biological activity when administered to a mammal including a human, which is interchangeable with the term "physiologically active protein", "active protein", "active polypeptide" or "peptide drug".

The term "protein conjugate" or "conjugate" refers to a compound comprising a physiologically active polypeptide, a non-peptidic polymer and an immunoglobulin which are covalently interlinked to one another in accordance with the present invention.

The term "complex", as distinguished from the term "conjugate", is used herein to mean those compounds comprising only two components selected from a physiologically active polypeptide, an immunoglobulin and a non-peptidic polymer.

The term "non-peptidic polymer" refers to a biocompatible polymer comprising at least two monomers, in which the monomers are linked together via any covalent bond other than a peptide bond.

In accordance with one aspect of the present invention, there is provided a protein conjugate comprising i) a physiologically active polypeptide, ii) a non-peptidic polymer, and iii) an immunoglobulin, which are covalently linked to one another, and having a prolonged in vivo half-life of the physiologically active polypeptide.

For example, the protein conjugate of the invention may comprise at least one unit structure of [active polypeptide/non-peptidic polymer/immunoglobulin], in which all of the components are covalently interlinked in a linear form. The non-peptidic polymer may have two reactive groups at both ends, through which the polymer is covalently linked to the physiologically active polypeptide and the immunoglobulin, respectively. In a preferred embodiment, two complexes of the physiologically active polypeptide and the non-peptidic polymer may be covalently linked to an immunoglobulin.

The molar ratio of the physiologically active polypeptide to the immunoglobulin may range from 1:1 to 10:1, preferably 1:1 to 4:1.

One kind of polymer as well as a combination of different kinds of polymers may be used as the non-peptidic polymer.

In the protein conjugate of the present invention, the suitable binding sites of the immunoglobulin may include a free functional group of an amino acid residue in the variable region or the constant region of the immunoglobulin. Suitable sites of the immunoglobulin for covalent bonding with the non-peptidic polymer or active polypeptide may include an amino-terminal group within the variable region, amine-group of lysine residue or histidine residue, and free —SH group of cysteine, and the suitable site of the non-peptidic polymer is a terminal reactive group.

The immunoglobulin may be selected from the group consisting of IgG, IgA, IgD, IgE, IgM, a combination thereof and all the subtypes of IgG such as IgG1, IgG2, IgG3 and IgG4. In order not to induce an immune response in a patient, the immunoglobulin is preferably a human immunoglobulin.

As a component constituting the protein conjugate of the invention, the immunoglobulin may be either a natural one isolated from the blood or a recombinant prepared by genetic engineering. Any immunoglobulin modified with substitution, deletion or addition of amino acid residues in various sites therein as well as any hyper-glycosylated, hypo-glycosylated or aglycosylated derivative thereof also may be used for the present invention, as long as such immunoglobulin or derivative is substantially equivalent to a wild-type in terms of the function, structure and stability thereof. Increase or decrease of the degree of glycosylation or deglycosylation may be carried out by any one of the conventional methods such as chemical, enzymatic and biotechnological methods. Amino acid residue Nos. 214 to 238, 297 to 299, 318 to 322, and 327 to 331 of an immunoglobulin G, which have been known as important sites for binding, may be used as a suitable site for the modification.

A suitable non-peptidic polymer has a reactive group selected from the group consisting of aldehyde, propionic aldehyde, butyl aldehyde, maleimide and succinimide derivative. The succinimide derivative may be selected from the group consisting of succinimidyl propionate, succinimidyl carboxymethyl, hydroxy succinimidyl and succinimidyl carbonate. A non-peptidic polymer having aldehyde groups at both ends is effective in minimizing non-specific coupling, thereby linking the non-peptidic polymer with a physiologically active polypeptide and an immunoglobulin at each end of the polymer, respectively. A protein conjugate produced by reductive alkylation of an aldehyde group is more stable than that coupled via an amide bond.

The reactive groups at the both ends of the non-peptidic polymer may be identical to or different from each other. For example, a non-peptidic polymer may have a maleimide group at one end, and a maleimide group, an aldehyde group or a propionic aldehyde group at the other end. When poly (ethylene glycol) is used as the non-peptidic polymer, a commercially available product may be used for preparing the protein conjugate of the invention, or the terminal hydroxy groups of the commercial PEG may be further converted to other reactive groups before the coupling reaction.

The non-peptidic polymer may serve as a spacer which covalently links the amino terminal, lysine residue, histidine residue or cysteine residue of the immunoglobulin and one of the reactive groups of the physiologically active polypeptide, respectively.

The non-peptidic polymer is preferably selected from the group consisting of poly(ethylene glycol), poly(propylene glycol), ethylene glycol-propylene glycol copolymer, polyoxyethylated polyol, polyvinyl alcohol, polysaccharide, dextran, polyvinyl ethyl ether, poly(lactic-glycolic acid), biodegradable polymer, lipid polymer, chitin, hyaluronic acids, and a combination thereof. Derivatives of the above known in the art may be used for the same purpose. More preferable non-peptidic polymer is poly(ethylene glycol). The molecular weight of the non-peptidic polymer may range from 500 to 100,000, preferably, 500 to 20,000.

Previously reported cross-linking agents for combining two polypeptides by gene cloning, such as oligopeptides, increase the possibility of undesired immune response and limit the binding site to N-terminal or C-terminal of the polypeptides. Accordingly, one advantage of the use of a non-peptidic polymer over the oligopeptides lies in the reduction of toxicity and immunogenicity. Another advantage is its broad applicability due to the diversity of the sites to be bound.

When used as a cross-linking agent, small chemical compounds such as carbodiimide and glutaraldehyde may result in denaturation of polypeptides to be linked therethrough, or may obstruct a controlled binding and purification of the resultant. Contrary to such chemicals, the protein conjugate of the invention, which comprises a non-peptidic polymer, is advantageous in terms of easiness of controlling the binding, purifying the resulting conjugates and minimizing non-specific coupling reaction.

The protein conjugate of the present invention shows a prolonged in vivo half-life and activity remarkably superior to a polypeptide-PEG complex or a polypeptide-PEG-albumin conjugate. According to pharmacokinetic analyses, the half-life of an hGH-PEG-IgG conjugate of the present invention was about thirteen times longer than that of wild-type hGH, while an hGH-PEG complex and an hGH-PEG-albumin conjugate show half-lives seven times and five times longer than the wild-type protein, respectively (see Test Example 2, Table 3). Similar results were obtained from tests using G-CSF, $^{17}$S-G-CSF, interferons or EPO instead of hGH. Compared with active polypeptide complexes modified with PEG only or a PEG-albumin complex, the protein conjugate of the present invention shows considerable increases in both mean residence time ("MRT") and serum half-life, which are higher by a factor of 2-70 than those of conventional complexes (see Test Example 2, Tables 4 to 7). Further, Fab'-PEG-IgG conjugates of the present invention, i.e., Fab'-S-PEG-N-IgG and Fab'-N-PEG-N-IgG conjugates wherein an IgG-PEG complex is linked to a SH group adjacent to the C-terminal of Fab' or to the N-terminal of Fab', respectively, show serum half-lives two to three times longer than that of a Fab'-S-40K PEG complex (see Test Example 3 and FIG. 12).

Figure 10:
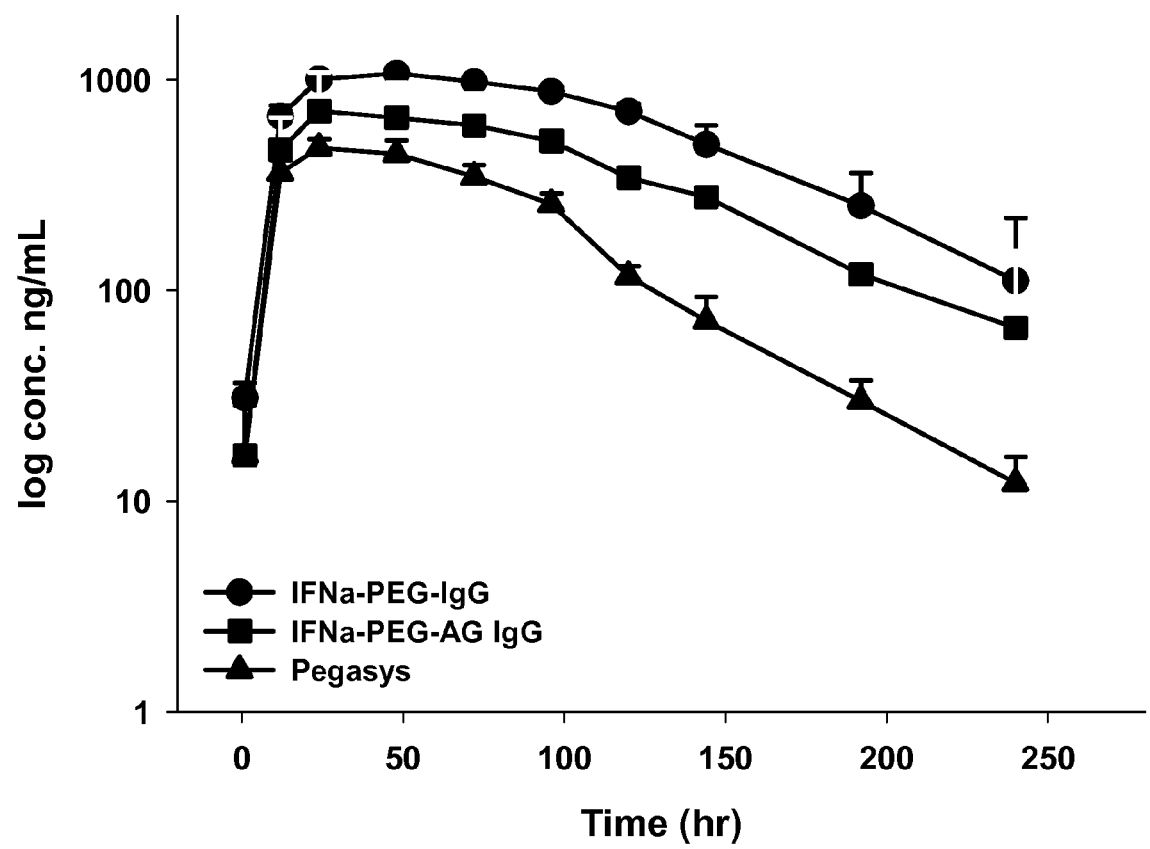
FIG. 10: a pharmacokinetic graph showing that IFN α-PEG-AG IgG conjugate has an enhanced blood stability as compared with the wild-type IFN α and maintains its activity despite the absence of the sugar chain.
Figure 11:
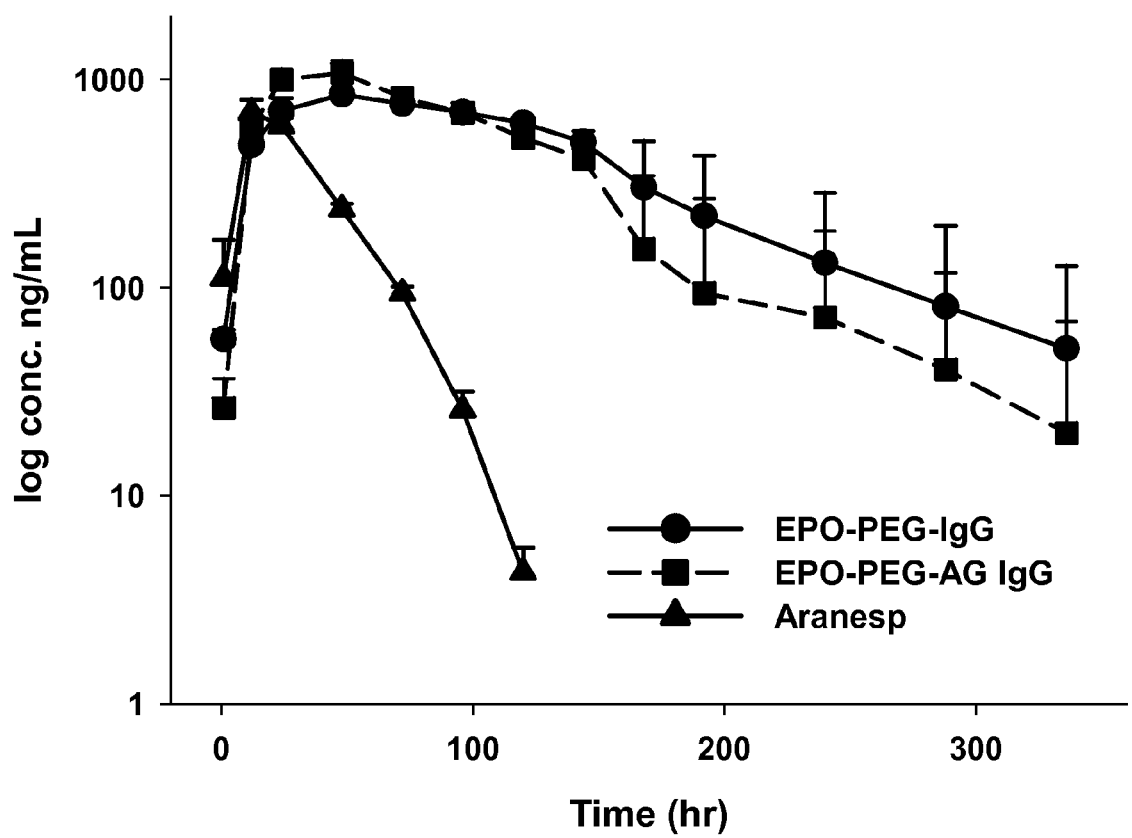
FIG. 11: a pharmacokinetic graph showing that EPO-PEG-AG IgG conjugate has an enhanced blood stability as compared with the wild-type IFN α and maintains its activity despite the absence of the sugar chain.

Further, the protein conjugates prepared by employing an aglycosylated immunoglobulin show blood half-lives and in vitro activities similar to those of the corresponding protein conjugates comprising glycosylated immunoglobulin (see Tables 4, 7 and 9, and FIGS. 10 and 11).

The results of pharmacokinetic analyses show that the protein conjugates of the present invention applied to various polypeptides including hGH, interferon, EPO, G-CSF or its derivative, and an antigen fragment exhibit excellent performance characteristics in terms of blood half-life and MRT, and, thus, can be advantageously employed in preparing a polypeptide drug formulation having a prolonged in vivo half-life.

Further, according to in vivo tests using animal models, the inventive hGH-PEG-IgG conjugate shows an excellent in vivo activity. Specifically, the effect generated by administering hGH-PEG-IgG conjugate once/6 days in an amount corresponding to a third of the wild-type dose is equal or better than daily administration of the wild-type, which means that the in vivo activity of hGH-PEG-IgG conjugate is more than 3-fold higher than that of the wild-type (see FIG. 14).

Figure 15:
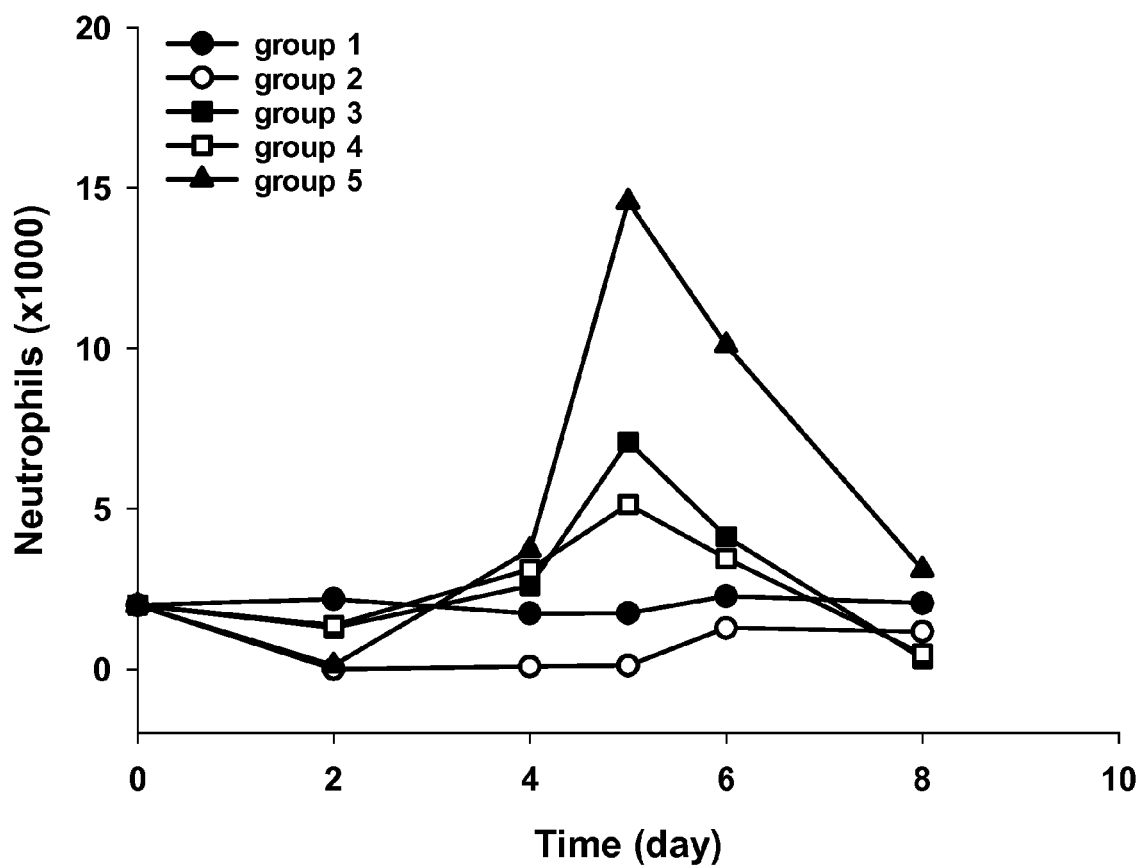
FIG. 15: In vivo activity of G-CSF-PEG-IgG conjugates based on the time-dependent change in the number of neutrophils: no treatment (group 1), vehicle injection only (group 2), wild-type G-CSF (group 3), 20 kDa PEG-G-CSF (group 4), and $^{17}$S-G-CSF-PEG-IgG conjugate treatment (group 5)
Figure 16:
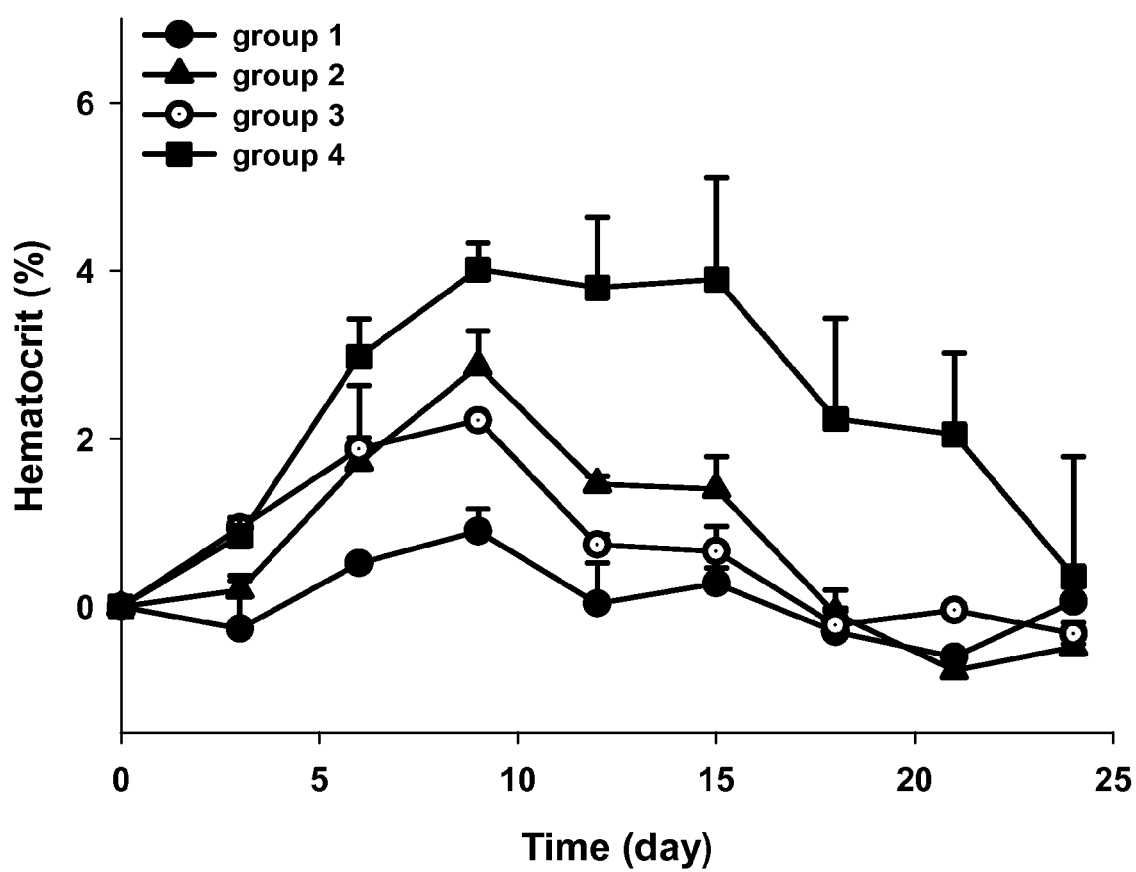
FIG. 16: In vivo activity of EPO-PEG-IgG conjugates based on the time-dependent change in the number of hematocrit: solvent injection only (group 1), wild-type EPO (group 2), highly glycosylated EPO (group 3), and EPO-PEG-IgG conjugate treatment (group 4).

The inventive $^{17}$S-G-CSF derivative-PEG-IgG conjugate exhibits an in vivo activity 3-fold higher than that of 20 kDa PEG-G-CSF complex, and, when administered once/5 days, it generates two-fold higher effect for recovering neutrophil than the wild-type G-CSF administered daily to the same total amount of administration (FIG. 15). Moreover, the inventive EPO-PEG-IgG conjugate induces a higher and faster rate of increase in the hematocrit level than the wild-type EPO and a highly glycosylated EPO, and maintains such a high in vivo activity for a long time (FIG. 16).

These results show that the protein conjugate of the present invention significantly increases the blood half-life and in vivo activity of a physiologically active polypeptide while overcoming the problem of the wild-type peptides which require frequent administration.

Exemplary classes of the physiologically active polypeptides include the following polypeptides, and muteins and other analogs thereof: hormone, cytokine, enzyme, antibody, growth factor, transcription regulatory factor, blood factor, vaccine, structural protein, ligand protein and receptor.

Specific examples of the physiologically active polypeptides suitable for preparing the protein conjugate of the invention include human growth hormone, growth hormone releasing hormone, growth hormone releasing peptide, interferons (e.g., interferons α, β and γ), colony stimulating factor, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, -28, -29 and -30), glucocerebrosidase, macrophage activating factor, macrophage peptide, B cell factor, T cell factor, protein A, suppressive factor of allergy, cell necrosis glycoprotein, immunotoxin, lymphotoxin, tumor necrosis factor, tumor inhibitory factor, transforming growth factor, alpha-1 antitrypsin, albumin, apolipoprotein-E, erythropoietin, hyper-glycosylated erythropoietin, factor VII, factor VIII, factor IX, plasminogen activator, urokinase, streptokinase, protein C, C-reactive protein, renin inhibitor, collagenase inhibitor, superoxide dismutase, leptin, platelet derived growth factor, epidermal growth factor, osteogenic growth factor, osteogenesis stimulating protein, calcitonin, insulin, atriopeptin, cartilage inducing factor, connective tissue activator protein, follicle stimulating hormone, luteinizing hormone, FSH releasing hormone, nerve growth factor, parathyroid hormone, relaxin, secretin, somatomedin, insulin-like growth factor, adrenocorticotrophic hormone, glucagon, cholecystokinin, pancreatic polypeptide, gastrin releasing peptide, corticotropin releasing factor, thyroid stimulating hormone, receptor (e.g., TNFR (P75) and TNFR (P55)), receptor antagonist (e.g., IL1-Ra), cell surface antigen (e.g., CD2, 3, 4, 5, 7, 11a, 11b, 18, 19, 20, 23, 25, 33, 38, 40, 45 and 69), monoclonal antibody, polyclonal antibody, antibody fragment, and virus-derived vaccine antigen.

The antibody fragment refers to a fragment of an antibody capable of binding to a specific antigen, e.g, Fab, Fab', F(ab')2, Fd and scFv, wherein Fab' is preferred. Fab fragment consists of the variable domains and the first constant domains ($C_H1$ domains) of the light and heavy chains of an antibody; Fab' fragment, a Fab fragment plus several amino acid residues containing one or more cystein residues from the hinge region, attached to the C-terminal of the $C_H1$ domain; F(ab')2 fragment, two Fab' fragments linked to each other by a disulfide bond or by a chemical reaction; and Fd fragment, variable region and the first constant domain ($C_H1$) of a heavy chain. scFv fragment is a single polypeptide chain consisting of variable regions of a heavy and a light chain linked with each other by a peptide linker.

A particularly preferred polypeptide is the one selected from the group consisting of human growth hormone, interferons (e.g., interferons α, β and γ), granulocyte colony stimulating factor and erythropoietin in light of the fact that these polypeptides need more frequent administration than others for the purpose of treating or preventing relevant diseases.

List of the physiologically active polypeptides, to which the present invention can be applied, is not limited to those recited in the above but includes any muteins or derivatives thereof inasmuch as the function, structure, activity and stability of the mutein or derivative can be recognized as an equivalent or superior to those of the wild-type polypeptides.

Another aspect of the present invention is to provide a method for preparing said protein conjugate, which comprises the steps of:
  (a) covalently linking at least one physiologically active polypeptide, at least one immunoglobulin with at least one non-peptidic polymer having reactive groups at both ends; and
  (b) isolating a protein conjugate comprising essentially the physiologically active polypeptide, the immunoglobulin and the non-peptidic polymer, which are interlinked covalently.

In step (a) of the above method, polypeptides, immunoglobulins and non-peptidic polymers may be covalently linked by a two-step reaction or a simultaneous reaction. The two-step reaction (e.g., a non-peptidic polymer is covalently linked to an active polypeptide or an immunoglobulin and, then, the resulting complex is covalently linked to an active polypeptide or an immunoglobulin to give a conjugate thereof, in which the active polypeptide and the immunoglobulin are linked to each other via the non-peptidic polymer) is advantageous in reducing the production of undesirable by-products.

Accordingly, the step (a) of the above method may comprise:
  (a1) covalently coupling one end of the non-peptidic polymer with either an immunoglobulin or a physiologically active polypeptide;
  (a2) isolating from the reaction mixture a complex comprising the non-peptidic polymer coupled with the immunoglobulin or the physiologically active polypeptide; and
  (a3) covalently coupling the free end of the non-peptidic polymer of the complex with the immunoglobulin or physiologically active polypeptide, to produce a protein conjugate in which the non-peptidic polymer covalently interlinks the physiologically active polypeptide and immunoglobulin.

The molar ratio of the physiologically active polypeptide to the non-peptidic polymer in step (a1) may preferably range from 1:2.5 to 1:5 and the molar ratio of the immunoglobulin to the non-peptidic polymer in step (a1), preferably from 1:5 to 1:10. The molar ratio of the complex obtained in step (a2) to the physiologically active polypeptide or immunoglobulin in step (a3) may range from 1:0.5 to 1:20, preferably, 1:1 to 1:5.

Steps (a1) and (a3) may be preferably performed in the presence of a reducing agent, which may be selected from the group consisting of sodium cyanoborohydride, sodium borohydride, dimethylamine borate and pyridine borate.

The procedures for conducting steps (a2) and (b) may be based on conventional methods used for purifying proteins, such as size exclusion chromatography, ion exchange chromatography, etc. and a combination thereof, in accordance with the extent of required purity and the properties of the resulting conjugate including molecular weight and electricity.

Still another aspect of the present invention is to provide a pharmaceutical composition of a physiologically active polypeptide having a prolonged in vivo half-life in comparison with unmodified polypeptides, which comprises the protein conjugate of the invention and a pharmaceutically acceptable carrier (excipient).

The pharmaceutical composition of the present invention can be administered via various routes including oral, transdermal, subcutaneous, intravenous and intramuscular introduction, and injection is more preferred. The composition of the invention may be formulated so as to provide a quick, sustained or delayed release of the active ingredient after it is administered to a patient, by employing any one of the procedures well known in the art. The formulation may be in the form of a tablet, pill, powder, sachet, elixir, suspension, emulsion, solution, syrup, aerosol, soft and hard gelatin capsule, sterile injectable solution, sterile packaged powder and the like. Examples of suitable carriers, excipients or diluents are lactose, dextrose, sucrose, sorbitol, mannitol, starches, gum acacia, alginates, gelatin, calcium phosphate, calcium silicate, polyvinylpyrrolidone, cellulose, methylcellulose, microcrystalline cellulose, water, methylhydroxybenzoates, propylhydroxybenzoates, talc, magnesium stearate and mineral oil. The formulation may additionally include fillers, anti-agglutinating agents, lubricating agents, wetting agents, flavoring agents, emulsifiers, preservatives and the like.

The amount of the active ingredient actually administered ought to be determined in light of various relevant factors including the condition to be treated, the chosen route of administration, the age, sex and body weight of the individual patient, and the severity of the patient's symptom, especially, the kind of active ingredient. Owing to the enhanced stability of a protein conjugate of the invention, the total number and frequency of the administration of the polypeptide drug formulation comprising the protein conjugate can be considerably reduced.

The present invention is further defined in the following Examples. It should be understood that these Examples, while indicating preferred embodiments of the invention, are given by way of illustration only and are not intended to limit the scope of the invention.

EXAMPLE 1

Preparation of hGH-PEG-IgG Conjugate I (Step 1) Preparation of hGH-PEG Complex Human growth hormone (hGH, M. W. 22 kDa) was dissolved in 100 mM phosphate buffer solution to a concentration of 5 mg/ml, and polyethylene glycol containing aldehyde groups at both ends (ALD-PEG-ALD, Shearwater Inc, USA) which has a molecular weight of 3.4 kDa was added to the resulting buffer solution in an amount corresponding to an hGH:PEG molar ratio of 1:1, 1:2.5, 1:5, 1:10 or 1:20. Sodium cyanoborohydride ($NaCNBH_3$, Sigma) was added thereto to a final concentration of 20 mM as a reducing agent, and the reaction mixture was stirred at 4° C. for 3 hours. To separate an hGH-PEG complex in which PEG is selectively linked to the terminal amino residue of hGH in a molar ratio of 1:1, the reaction mixture was subjected to Superdex® (Pharmacia, USA) size exclusion chromatography. The hGH-PEG complex was eluted and purified from the column with 10 mM potassium phosphate buffer (pH 6.0) to remove contaminants such as unmodified hGH, unreacted PEG and dimeric by-products having two molecules of hGH linked at both ends of PEG. The purified hGH-PEG complex was concentrated to 5 mg/ml. It has been found that an optimal hGH:PEG molar ratio for obtaining the best result was in the range of 1:2.5 to 1:5.

(Step 2) Formation of Conjugate Between hGH-PEG Complex and IgG

Immunoglobulin G (IgG, Green Cross, Korea) having a molecular weight of 150 kDa was dissolved in 100 mM phosphate buffer solution. To conjugate IgG to the aldehyde group of the PEG-hGH complex purified in Example 1, the PEG-hGH complex was added to an IgG-containing buffer solution in an amount corresponding to an hGH-PEG complex:IgG molar ratio of 1:1, 1:2, 1:4 or 1:8. $NaCNBH_3$ was added thereto to a final concentration of 20 mM as a reducing agent, and the reaction mixture was gently stirred at 4° C. for 20 hours. To purify the hGH-PEG-IgG conjugate from contaminants after the conjugation reaction, the reaction mixture was subjected to anion exchange chromatography using a DEAE column (Pharmacia, USA) equilibrated with 20 mM Tris buffer solution (pH 7.5). The mobile phase was changed from Buffer A (20 mM Tris buffer, pH 7.5) to Buffer B (20 mM Tris buffer containing 1.0 M NaCl, pH 7.5) with a linear concentration gradient (NaCl concentration: 0 M→0.5 M). To remove small quantities of unreacted IgG and unmodified hGH from the eluted hGH-PEG-IgG conjugate, the eluting solution was subjected to cation exchange chromatography using a polyCAT column (PolyLC, USA) equilibrated with 10 mM sodium acetate (pH 4.5). The mobile phase was changed from Buffer A (10 mM sodium acetate, pH 4.5) to Buffer B (10 mM sodium acetate containing 1.0 M NaCl, pH 7.5) in a linear fashion (NaCl concentration: 0 M→0.5 M), which results in purifying the hGH-PEG-IgG conjugate (FIG. 1).

It has been found that the optimal hGH-PEG complex:IgG molar ratio for obtaining the best result was 1:4.

EXAMPLE 2

Preparation of hGH-PEG-IgG Conjugate II (Step 1) Preparation of IgG-PEG Complex IgG (Green Cross, Korea) was dissolved in 100 mM phosphate buffer to a concentration of 15 mg/ml, and 3.4 kDa of ALD-PEG-ALD (Shearwater Inc, USA) was added to the resulting buffer solution in an amount corresponding to an IgG:PEG molar ratio of 1:1, 1:2.5, 1:5, 1:10 or 1:20. $NaCNBH_3$ was added thereto to a final concentration of 20 mM as a reducing agent, and the reaction mixture was stirred at 4° C. for 3 hours. To separate IgG-PEG complex in which PEG is selectively linked to the terminal amino residue of IgG in a molar ratio of 1:1, the reaction mixture was subjected to Superdex® (Pharmacia, USA) size exclusion chromatography. The IgG-PEG complex was eluted and purified from the column with 10 mM potassium phosphate buffer (pH 6.0) to remove contaminants such as unmodified IgG, unreacted PEG and dimeric by-products having two molecules of IgG linked at both ends of PEG. The purified IgG-PEG complex was concentrated to 15 mg/ml. It has been found that an optimal IgG:PEG molar ratio for obtaining the best result was in the range of 1:5 to 1:10.

(Step 2) Formation of Conjugate Between IgG-PEG Complex and hGH

To conjugate hGH (M. W. 22 kDa) to the IgG-PEG complex purified in Example 1, hGH dissolved in 100 mM phosphate buffer was reacted with the IgG-PEG complex in a molar ratio of 1:1, 1:1.5, 1:3 or 1:6. $NaCNBH_3$ was added thereto to a final concentration of 20 mM as a reducing agent, and the reaction mixture was stirred at 4° C. for 20 hours. The reaction mixture was subjected to purification according to the same method described in step 2 of Example 1 to remove unreacted substances and by-products, and the IgG-PEG-hGH conjugate was purified therefrom.

EXAMPLE 3

Preparation of IFN α-PEG-IgG Conjugate

An IFN α-PEG-IgG conjugate was prepared and purified according to the same method described in Example 1, except that interferon alpha 2b (IFN α 2b, M. W. 20 kDa) was employed instead of hGH and the IFN α 2b:ALD-PEG-ALD (M. W. 3.4 kDa) molar ratio was 1:5.

EXAMPLE 4

Preparation of Human G-CSF-PEG-IgG Conjugate

A G-CSF-PEG-IgG conjugate was prepared and purified according to the same method described in Example 1, except that human granulocyte colony stimulating factor (G-CSF, M. W. 18.7 kDa) was employed instead of hGH and the G-CSF:ALD-PEG-ALD (M. W. 3.4 kDa) molar ratio was 1:5.

Further, G-CSF derivative-PEG-IgG conjugate was prepared and purified according to the same method described above using G-CSF derivative ($^{17}$S-G-CSF) which was attained by replacing the $17^{th}$ amino acid of wild-type G-CSF with serine.

EXAMPLE 5

Preparation of EPO-PEG-IgG Conjugate

An EPO-PEG-IgG conjugate was prepared and purified according to the same method described in Example 1, except that human erythropoietin (EPO, M. W. 35 kDa) was employed instead of hGH and the EPO:ALD-PEG-ALD (M. W. 3.4 kDa) molar ratio was 1:5.

EXAMPLE 6

Preparation of Protein Conjugate Using PEG Having a Different Functional Group hGH-PEG-IgG conjugates were prepared as follows, using a PEG having different functional groups other than aldehyde groups at both ends thereof. 10 mg of hGH dissolved in 100 mM phosphate buffer was reacted with PEG containing succinimidyl propionate (SPA) groups at both ends (SPA-PEG-SPA, Shearwater Inc, USA, M. W. 3.4 kDa) in an amount corresponding to an hGH:PEG molar ratio of 1:1, 1:2.5, 1:5, 1:10 or 1:20. The reaction mixture was stirred at room temperature for 2 hours. To obtain an hGH-PEG complex in which PEG is selectively linked to the lysine residue of hGH in a molar ratio of 1:1, the reaction mixture was subjected to Superdex® (Pharmacia, USA) size exclusion chromatography. The hGH-PEG complex was eluted and purified from the column with 10 mM potassium phosphate buffer (pH 6.0) to remove contaminants such as unmodified hGH, unreacted PEG and dimeric by-products having two molecules of hGH linked at both ends of PEG The purified hGH-PEG complex was concentrated to 5 mg/ml. An hGH-PEG-IgG conjugate was prepared using the concentrated hGH-PEG complex according to the same method described in Example 1. It has been found that an optimal hGH:PEG molar ratio for obtaining the best result was in the range of 1:2.5 to 1:5.

Another hGH-PEG-IgG conjugate was prepared and purified according to the same method described above, except that PEG containing N-hydroxysuccinimidyl (NHS) groups at both ends (NHS-PEG-NHS, Shearwater Inc, USA) was employed instead of SPA-PEG-SPA.

EXAMPLE 7

Preparation of Protein Conjugate Using PEG Having a Different Molecular Weight An hGH-PEG complex was prepared and purified according to the same method described in step 1 of Example 1, except that PEG containing aldehyde groups at both ends and having a molecular weight of 10,000 daltons (ALD-PEG-ALD, Shearwater Inc, USA) was employed. At this time, it has been found that an optimal hGH:PEG molar ratio for obtaining the best result was in the range of 1:2.5 to 1:5. The purified hGH-PEG complex was concentrated to 5 mg/ml. An hGH-PEG-IgG conjugate was prepared using the concentrated hGH-PEG complex according to the same method described in step 2 of Example 1.

EXAMPLE 8

Preparation of Fab'-S-PEG-N-IgG Conjugate (—SH group)

(Step 1) Expression and Purification of Fab'

*Escherichia coli* BL21/poDLHF (Deposit No.: KCCM 10511) expressing anti-TNF-αFab'was inoculated in 100 ml of LB medium and cultured overnight with shaking. The cultured LB broth was transferred to a 5 l fermenter (Marubishi) and cultured under the condition of temperature 30° C., aeration rate 20 vvm, stirring speed 500 rpm. With the progress of the fermentation, suitable amounts of glucose and a yeast extract were added to the culture for supplementing the shortage of energy sources caused by the growth of the microorganisms. When the absorbance at 600 nm of the cultured broth reached 80, IPTG was added to the culture to induce the protein expression. The cultivation was continued for additional 40 to 45 hours until the absorbance at 600 nm of the cultured broth reached 120 to 140. The resulting cultured broth was centrifuged at 20,000×g for 30 minutes to obtain a supernatant.

The supernatant was subjected to the following three-step chromatographic purification process for the purification of anti-TNF-α Fab'. The supernatant was loaded on a HiTrap Protein G (5 ml, Pharmacia, Germany) column equilibrated with 20 mM phosphate buffer (pH 7.0), and eluted with 100 mM glycine buffer (pH 3.0). Eluted Fab' fraction was loaded on a Superdex 200 column (Pharmacia, Germany) equilibrated with 10 mM phosphate buffered saline (PBS, pH 7.3), and eluted with the same buffer. Eluted Fab' fraction was loaded on a polyCAT 21×250 (PolyLC Inc., USA) and eluted with 10 mM acetate buffer (pH 4.5) under a linear concentration gradient of NaCl (0.15 M->0.4 M) to obtain a pure anti-TNF-α Fab' fraction.

(Step 2) Preparation of an IgG-PEG Complex 150 mg of immunoglobulin G (IgG, M. W. 150 kDa, Green Cross Inc., Korea) was dissolved in 100 mM PBS (pH 6.0) to a concentration of 5 mg/ml, and NHS-PEG-MAL (M.W. 3400 Da, Shearwater Inc., USA) was added to the resulting solution in an amount corresponding to an IgG:PEG molar ratio of 1:10. The reaction mixture was gently stirred at 4° C. for 12 hours.

Upon completion of the reaction, the reaction buffer was changed to 20 mM PBS (pH 6.0) to remove unreacted NHS-PEG-MAL. Thereafter, the reaction mixture was loaded on a polyCAT 21×250 column (PolyLC Inc., USA) and eluted with 20 mM PBS (pH 6.0) using a linear concentration gradient method (NaCl concentration 0.15 M->0.5 M) to obtain an IgG-PEG complex. The unreacted IgG was eluted later than the IgG-PEG complex and discarded.

(Step 3) Preparation of Fab'-S-PEG-N-IgG Conjugate (—SH Group)

Purified Fab' obtained in step 1 was dissolved in 100 mM PBS (pH 7.3) to a concentration of 2 mg/ml, and IgG-PEG complex prepared in Step 2 was added to the resulting solution in an amount corresponding to Fab':complex molar ratio of 1:5. The reaction mixture was concentrated to a protein concentration of 50 mg/ml and the concentrate was gently stirred at 4° C. for 24 hours.

Upon completion of the coupling reaction, the reaction mixture was loaded on a Superdex 200 column (Pharmacia, USA) equilibrated with 10 mM PBS (pH 7.3), and eluted with the same buffer at a flow rate of 1 ml/min to obtain an Fab'-S-PEG-N-IgG conjugate fraction. The Fab'-S-PEG-N-IgG conjugate having a high molecular weight eluted early, and the unreacted IgG-PEG complex and Fab' were eluted later than the conjugate and discarded. In order to remove the remaining unreacted IgG-PEG complex, the Fab'-S-PEG-N-IgG conjugate fraction was loaded on a polyCAT 21×250 column (PolyLC Inc., USA), and eluted with 20 mM PBS (pH 6.0) using a linear concentration gradient method (NaCl concentration: 0.15 M->0.5 M). Consequently, a fraction containing pure Fab'-S-PEG-N-IgG conjugate was obtained, wherein the IgG-PEG complex was linked to the —SH group adjacent to the C-terminal of the Fab'.

EXAMPLE 9

Preparation of Fab'-N-PEG-N-IgG Conjugate (N-terminal)

(Step 1) Preparation of Fab'-PEG Complex (N-terminal)

40 mg of purified Fab' obtained in step 1 of Example 8 was dissolved in 100 mM PBS (pH 6.0) to a concentration of 5 mg/ml, and ButylALD-PEG-ButylALD (M.W. 3400 Da, Shearwater Inc., USA) was added to the resulting solution in an amount corresponding to an Fab':PEG molar ratio of 1:5. NaCNBH$_3$ was added thereto to a final concentration of 20 mM as a reducing agent, and the reaction mixture was gently stirred at 4° C. for 2 hours.

Upon completion of the reaction, the buffer was changed to 20 mM PBS (pH 6.0). After the change of the buffer, the mixture was loaded on a polyCAT 21×250 column (PolyLC Inc., USA) and eluted with 20 mM PBS (pH 4.5) using a linear concentration gradient method (NaCl concentration: 0.15 M→0.4 M) to obtain a fraction containing a Fab'-PEG complex. The unreacted Fab' was eluted later than the complex and discarded.

(Step 2) Preparation of Fab'-N-PEG-N-IgG Conjugate (N-terminal)

Purified Fab'-PEG complex obtained in step 1 was dissolved in 100 mM PBS (pH 6.0) to a concentration of 10 mg/ml, and IgG (M. W. 150 kDa, Green Cross Inc., Korea) was added to the resulting solution in an amount corresponding to the complex:IgG molar ratio of 1:5. The reaction mixture was concentrated to a protein concentration of 50 mg/ml. NaCNBH$_3$ was added thereto to a final concentration of 20 mM as a reducing agent, and the reaction mixture was gently stirred at 4° C. for 24 hours.

Upon completion of the coupling reaction, the reaction mixture was loaded on a Superdex 200 column (Pharmacia, USA) equilibrated with 10 mM PBS (pH 7.3), and eluted with the same buffer at a flow rate of 1 ml/min to obtain a fraction containing a Fab'-N-PEG-N-IgG conjugate. The Fab'-N-PEG-N-IgG conjugate having a high molecular weight eluted early, and the unreacted immunoglobulin and Fab'-PEG complex were eluted later than the conjugate and discarded. In order to remove the remaining unreacted immunoglobulin, the Fab'-N-PEG-N-IgG conjugate fraction was loaded on a polyCAT 21×250 column (PolyLC Inc., USA), and eluted with 20 mM PBS (pH 6.0) using a linear concentration gradient method (NaCl concentration: 0.15 M→0.5 M). Consequently, a fraction containing pure Fab'-N-PEG-N-IgG conjugate was obtained, wherein the IgG-PEG complex was linked to the N-terminal of Fab'.

EXAMPLE 10

Preparation of Aglycosylated IgG(AG IgG)

200 mg of immunoglobulin G (Green Cross Inc., Korea) was dissolved in 100 mM phosphate buffer (pH 7.5) to a concentration of 2 mg/, and 300 U/mg of an aglycosylase, PNGase F (NEB Inc., UK) was added thereto. The mixture was reacted at 37° C. for 24 hours with gentle stirring. Upon the completion of the reaction, the reaction mixture was loaded on a SP sepharose FF (Pharmacia, Germany) column, and eluted with 10 mM acetate buffer (pH 4.5) using a linear concentration gradient method using 1 M NaCl (NaCl concentration: 0.1 M→0.6 M) to obtain a fraction of aglycosylated IgG, which was eluted later than the wild-type IgG.

EXAMPLE 11

Preparation of IFN α-PEG-AG IgG Conjugate

An IFN α-PEG-AG IgG conjugate was prepared as follows, by conjugating the aglycosylated IgG (AG IgG) prepared in Example 10 to an INF α-PEG complex prepared in Example 3.

The AG IgG (M.W.: about 147 kDa) was dissolved in 10 mM phosphate buffer. The IFN α-PEG complex was added to the AG IgG-containing buffer in an amount corresponding to the IFN α-PEG complex:AG IgG molar ratio of 1:1, 1:2, 1:4 or 1:8. The resulting mixture was adjusted to 100 mM phosphate buffer, and NaCNBH$_3$ was added thereto to a final concentration of 20 mM as a reducing agent. The reaction mixture was gently stirred at 4° C. for 20 hours. It has been found that the optimal IFN α-PEG complex:AG IgG molar ratio for obtaining the best result was 1:2.

To purify the IFN α-PEG-AG IgG conjugate from contaminants after the conjugation reaction, the reaction mixture was subjected to a size exclusion chromatography. The reaction mixture was loaded on an Superdex® (Pharmacia, USA) column and eluted with 10 mM PBS (pH 7.3) at a flow rate of 2.5 ml/min to obtain a fraction of the IFN α-PEG-AG IgG conjugate and also to remove contaminants such as unreacted AG IgG and IFN α-PEG complex. The fraction of the IFN α-PEG-AG IgG conjugate thus obtained was further subjected to cation exchange chromatography to remove small amounts of unreacted AG IgG and IFN α-PEG complex. The fraction was loaded on a polyCAT LP column (PolyLC, USA) equilibrated with 10 mM sodium acetate buffer (pH 4.5) and eluted with 10 mM sodium acetate buffer (pH 4.5) containing 1.0 M NaCl using a linear concentration gradient method (NaCl concentration: 0 M→0.6 M) to obtain a fraction of the IFN α-PEG-AG IgG conjugate. The fraction thus obtained was further subjected to anion exchange chromatography. The fraction was loaded on a PolyWAX LP column (PolyLC Inc., USA) equilibrated with 10 mM Tris-HCl buffer (pH 7.5) and eluted with 10 mM Tris-HCl buffer (pH 7.5) containing 1.0 M NaCl by a linear concentration gradient method (NaCl concentration: 0 M→0.3 M) to obtain a pure IFN α-PEG-AG IgG conjugate.

EXAMPLE 12

Preparation of EPO-PEG-AG IgG Conjugate

The procedure of Example 11 was repeated by employing the EPO-PEG complex prepared in Example 5 and the aglycosylated IgG prepared in Example 10 to obtain an EPO-PEG-AG IgG conjugate.

COMPARATIVE EXAMPLE 1

Preparation of PEG-hGH Complex 5 mg of hGH was dissolved in 100 mM potassium phosphate buffer (pH 6.0) to obtain 5 ml of a solution, and an activated methoxy-PEG-ALD having 40 kDa of PEG was added to the solution in an amount corresponding to an hGH:PEG molar ratio of 1:4. NaCNBH$_3$ was added thereto to a final concentration of 20 mM as a reducing agent, and the reaction mixture was gradually stirred at 4° C. for 18 hours. Then, ethanolamine was added thereto to a final concentration of 50 mM to inactivate unreacted PEG.

To further remove unreacted PEG, the reaction mixture was subjected to Sephadex® G-25 column (Pharmacia, USA)

chromatography. The column was equilibrated with 2 column volume (CV) of 10 mM Tris-HCl (pH 7.5) buffer before loading the reaction mixture. Elution fractions were analyzed for the absorbance at 260 nm using a UV spectrophotometer. The PEG modified hGH which has a large molecular weight was eluted first before unreacted PEG.

The PEG-modified hGH was further purified from the elution fraction as following. A column packed with 3 ml of PolyWAX LP (Polywax Inc, USA) was equilibrated with 10 mM Tris-HCl (pH 7.5) buffer. The elution fraction containing the PEG modified hGH was loaded to the column at a flow rate of 1 mL/min, and the column was washed with 15 ml of the equilibration buffer. Tri-, di- and mono-PEG linked hGHs were fractionated in order by a salt concentration gradient method (NaCl concentration: 0%→100%) using 1 M NaCl buffer for 30 min.

To further purify the mono-PEG linked hGH complex from the mixture, the column effluent was subjected to size exclusion chromatography. The concentrated effluent was loaded onto a Superdex 200 (Pharmacia, USA) column equilibrated with 10 mM sodium phosphate buffer and eluted with the same buffer solution at a flow rate of 1 ml/min. The tri- and di-PEG linked hGH complexes which eluted earlier than the mono-PEG linked hGH complex were removed to obtain purified mono-PEG linked hGH complex.

PEG-IFN, PEG-$^{17}$S-G-CSF derivative and PEG-G-CSF in which 40 kDa PEG is linked to the terminal amino residues of IFN α and G-CSF, respectively, were prepared and purified according to the same method described above.

COMPARATIVE EXAMPLE 2

Preparation of Albumin-hGH Complex

To conjugate albumin with the hGH-PEG complex obtained in Example 1, human serum albumin (HSA, M.W. about 67 kDa,) (Green Cross, Korea) dissolved in 10 mM phosphate buffer solution was reacted with the hGH-PEG complex in an amount corresponding to an hGH-PEG complex:HSA molar ratio is 1:1, 1:2, 1:4 or 1:8. The reaction mixture was concentrated to 100 mM phosphate buffer, and NaCNBH$_3$ was added thereto to a final concentration of 20 mM as a reducing agent. The reaction mixture was stirred at 4° C. for 20 hours. It has been found that an optimal hGH-PEG complex:albumin molar ratio for obtaining the best result was 1:2.

After the conjugation reaction, the reaction mixture was subjected to Superdex size exclusion chromatography to remove unreacted starting materials and by-products. The reaction mixture was concentrated and loaded onto the column at a flow rate of 2.5 ml/min using 10 mM sodium acetate (pH 4.5) to obtain purified hGH-PEG-albumin conjugate. Since the purified hGH-PEG-albumin conjugate was still contaminated by small quantities of unreacted albumin and hGH dimmer, cation exchange chromatography was further performed to remove these contaminants. The hGH-PEG-albumin conjugate effluent was loaded onto a SP5PW (Waters, USA) column equilibrated with 10 mM sodium acetate (pH 4.5), and fractionated with 10 mM sodium acetate (pH 4.5) containing 1.0 M NaCl with a linear concentration gradient (NaCl concentration: 0 M→0.5 M), to recover pure hGH-PEG-albumin.

IFN α-PEG-albumin, G-CSF-PEG-albumin and $^{17}$S-G-CSF derivative-PEG-albumin in which albumin is linked to IFN α, $^{17}$S-G-CSF and G-CSF, respectively, were prepared and purified according to the same method described above.

COMPARATIVE EXAMPLE 3

Preparation of Fab'-S-40K PEG Complex

The purified Fab' obtained in step 1 of Example 8 was placed in an activation buffer (20 mM PBS (pH 4.0) and 0.2 mM DTT) for 1 hour to activate the free —SH groups thereof. The buffer was changed to a PEGylation buffer (50 mM potassium phosphate (pH 6.5)). Maleimide-PEG (M. W. 40 kDa, Shearwater Inc., USA) was added to the resulting solution in an amount corresponding to Fab':PEG molar ratio of 1:10. The reaction mixture was stirred gently at 4° C. for 24 hours.

Upon completion of the reaction, the reaction mixture was loaded on a Superdex 200 column (Pharmacia, USA) equilibrated with 10 mM PBS (pH 7.3), and eluted with the same buffer at a flow rate of 1 ml/min to obtain a fraction containing a Fab'-S-40K PEG complex. The unreacted Fab' was eluted later than the complex and discarded. In order to remove unreacted Fab', the Fab'-S-40K PEG complex fraction was loaded on a polyCAT 21×250 column (PolyLC Inc., USA), and eluted with 20 mM PBS (pH 4.5) using a linear concentration gradient method (NaCl concentration: 0.15 M->0.5 M). Consequently, a fraction containing pure Fab'-S-40K PEG complex was obtained, wherein 40 kDa PEG was linked to the —SH group adjacent to the C-terminal of Fab'.

TEST EXAMPLE 1

Confirmation and Quantification of Protein Conjugates (1) Confirmation of Protein Conjugates Protein conjugates prepared in above Examples were analyzed for their modification state by SDS-PAGE using a gel having a concentration gradient of 4 to 20% and ELISA (R&D System, USA).

hGH, hGH-PEG, IFN and IFN-PEG were each developed on SDS-PAGE and a mixture with 50 mM DTT (dithiothreitol), while IgG, hGH-PEG-IgG and IFN-PEG-IgG without DTT.

Figure 2:
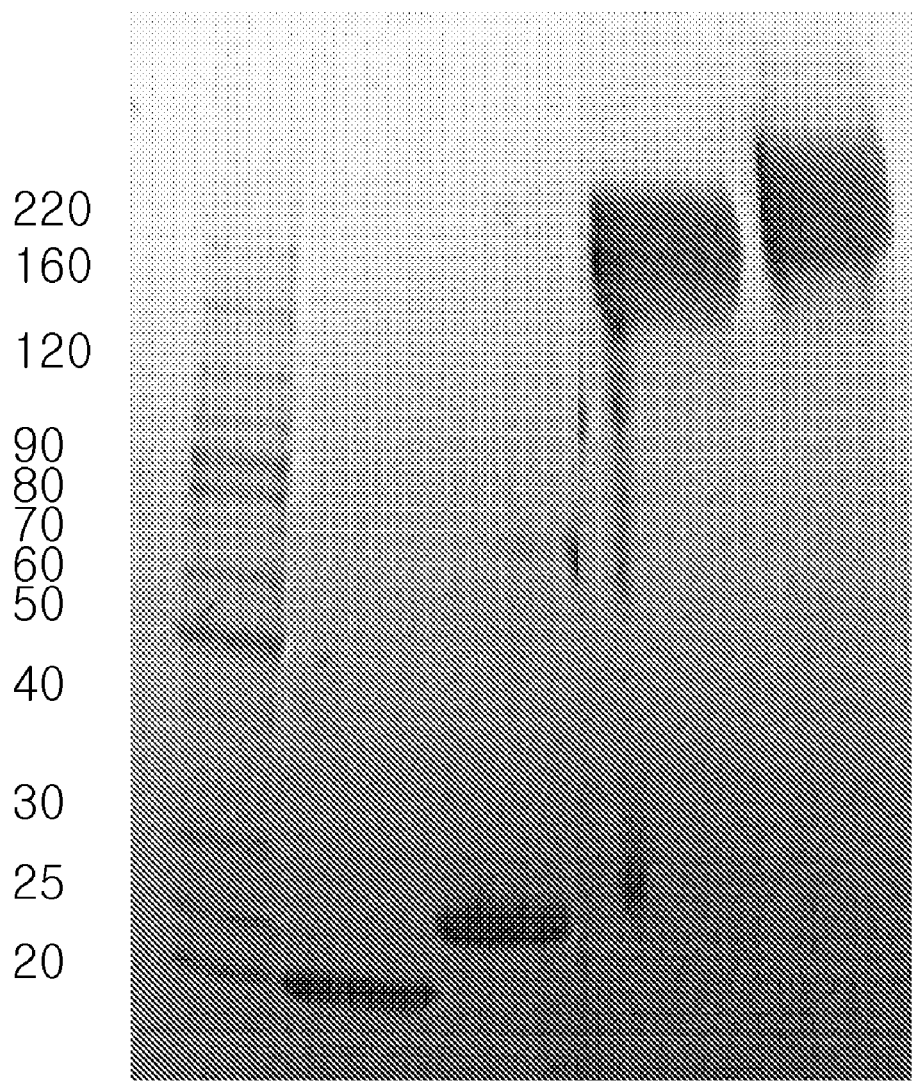
FIG. 2: SDS-PAGE results of hGH-PEG-IgG conjugates.
Figure 3:
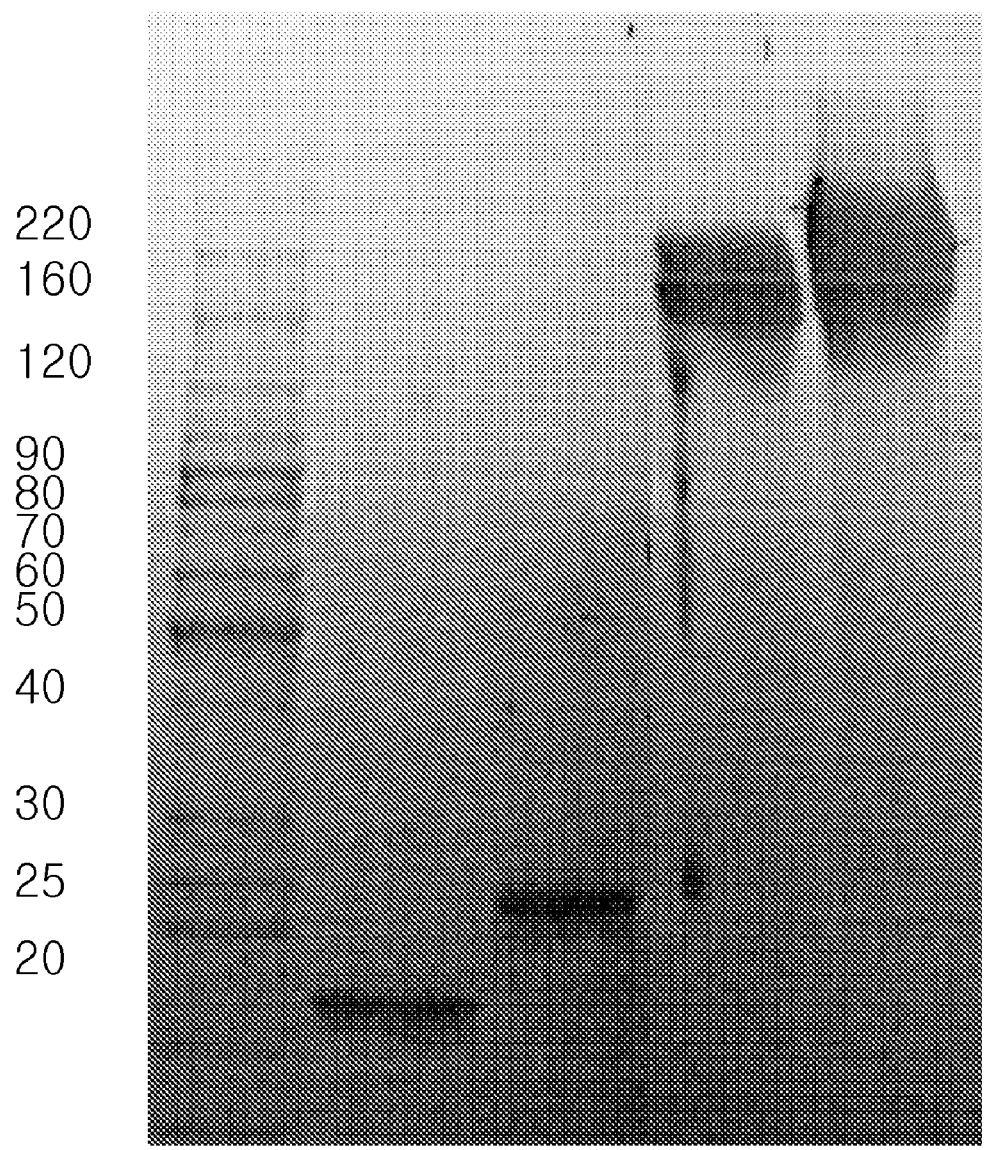
FIG. 3: SDS-PAGE results of Interferon-PEG-IgG conjugates.

FIGS. 2 and 3 show the SDS-PAGE results obtained for the hGH-PEG-IgG and IFN-PEG-IgG conjugates, respectively. Numbers listed on left margin are molecular weight markers (kDa).

Figure 4:
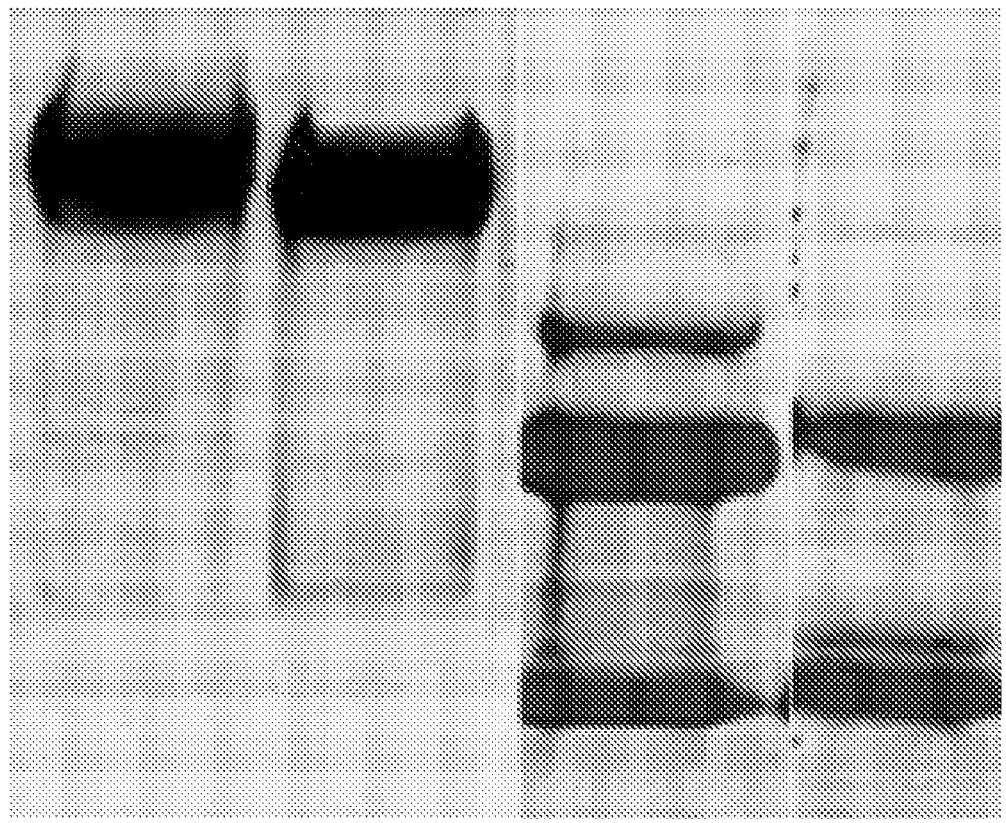
FIG. 4: SDS-PAGE results of hGH-PEG-IgG conjugates before and after the treatment of DDT.

As shown in FIG. 2, the apparent molecular weight of hGH-PEG-IgG conjugate is about 170 kDa. However, since it is difficult to discriminate the molecular weight difference between the IgG protein conjugates and wild-type IgG in SDS-PAGE, the hGH-PEG-IgG conjugate and IgG were reduced by DTT treatment, separated into heavy- and light-chains, and confirmed its conjugated state by SDS-PAGE, respectively (FIG. 4).

When IgG was treated with DTT, the light chain of IgG was separated first, and the heavy chain of IgG, later according to their molecular weight. Bands of hGH-PEG-IgG conjugate treated with DTT appeared at positions corresponding to molecular weights calculated by adding the molecular weight of hGH-PEG (3.4 kDa) to the molecular weight of light- and heavy chain fragments, respectively. The light chain of hGH-PEG-IgG conjugate formed a band at a lower position (smaller molecular weight) than the heavy chain of hGH-PEG-IgG conjugate whose band was found at a position corresponding to about 80 kDa. From the above results, it has been found that hGH coupled with light and heavy chains with equal probability, and that IgG reacts with hGH in a molar ratio of 1:1.

(2) Quantitative Analysis of Protein Conjugates

The amount of each protein conjugate prepared in the above Examples was determined by calculating the peak area of the conjugate observed in a size exclusion chromatography (column: Superdex, elution solution: 10 mM potassium phosphate buffer (pH 6.0)) and comparing it with that of the control. After conducting size exclusion chromatography using pre-quantified hGH, IFN, G-CSF, $^{17}$S-G-CSF, EPO and IgG, respectively, relative response factors of the peak areas were determined. The size exclusion chromatography was performed using a constant amount of each protein conjugate with a same condition, and the quantitative value of biologically active protein existed in each protein conjugate was determined by subtracting the peak area corresponding to IgG from the peak area of each protein conjugate obtained above.

ELISA (R&D System, USA) analysis was also carried out besides chromatography. If a portion of IgG is conjugated to a biologically active site of a polypeptide, the value obtained by ELISA using an antibody specific for the biologically active site would be lower than the value calculated by chromatography. In case of the hGH-PEG-IgG conjugate, it has been found that the value measured by ELISA was only about 30% of the value determined by chromatography.

(3) Confirmation of Purity and Mass of Protein Conjugates

Figure 5:
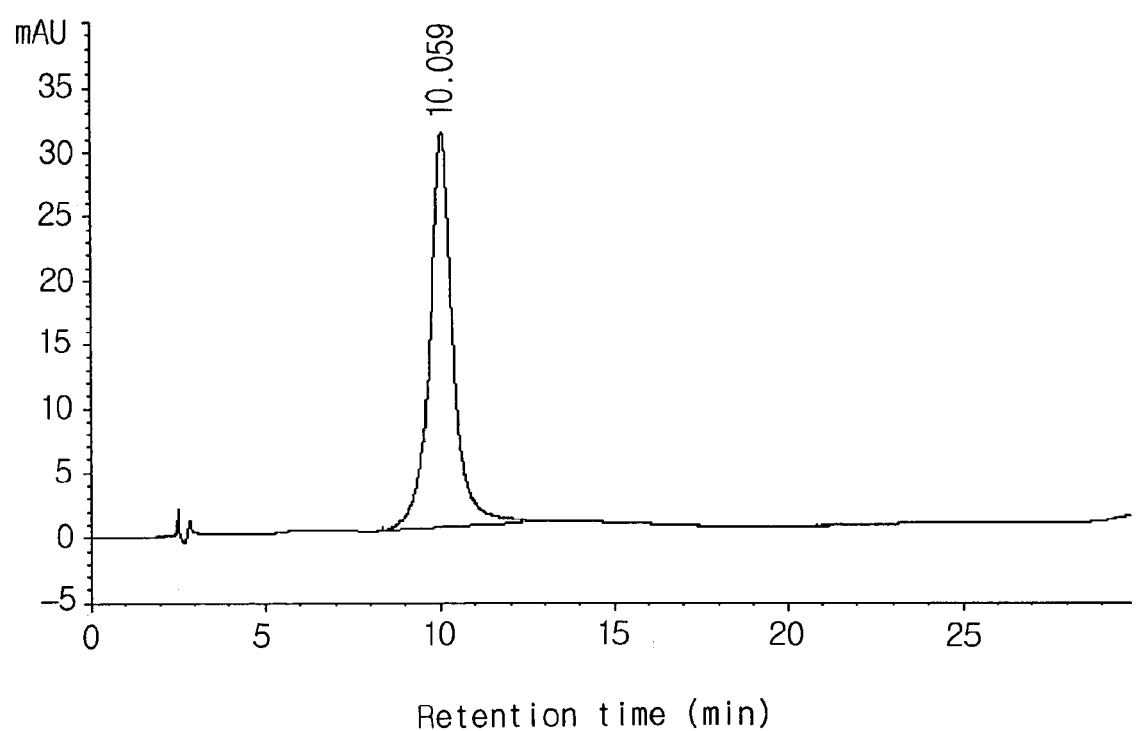
FIG. 5: Reverse-phase HPLC chromatogram of an IFN α-PEG-IgG conjugate.

In order to examine the purity of INF α-PEG-IgG complex obtained in Example 3, a reverse-phase HPLC was carried out using a reverse-phase column (259 VHP54 column, Vydac Inc., USA). The complex was eluted with acetonitrile by a linear concentration gradient method (acetonitrile concentration: 40%→100%) under the presence of 0.5% TFA and detected at 280 nm. As can be seen from FIG. 5, the purity of the complex is over 95%.

The protein conjugate obtained in each Example was analyzed for its absorbance value at 280 nm during size exclusion chromatography, and found that hGH-PEG-IgG, IFN-PEG-IgG, G-CSF and $^{17}$S-G-CSF-PEG-IgG each showed a single peak corresponding to a molecular weight of from 170,000 to 180,000 daltons. The peak of EPO-PEG-IgG was observed at a position corresponding to a molecular weight of 200,000 daltons.

Figure 6:
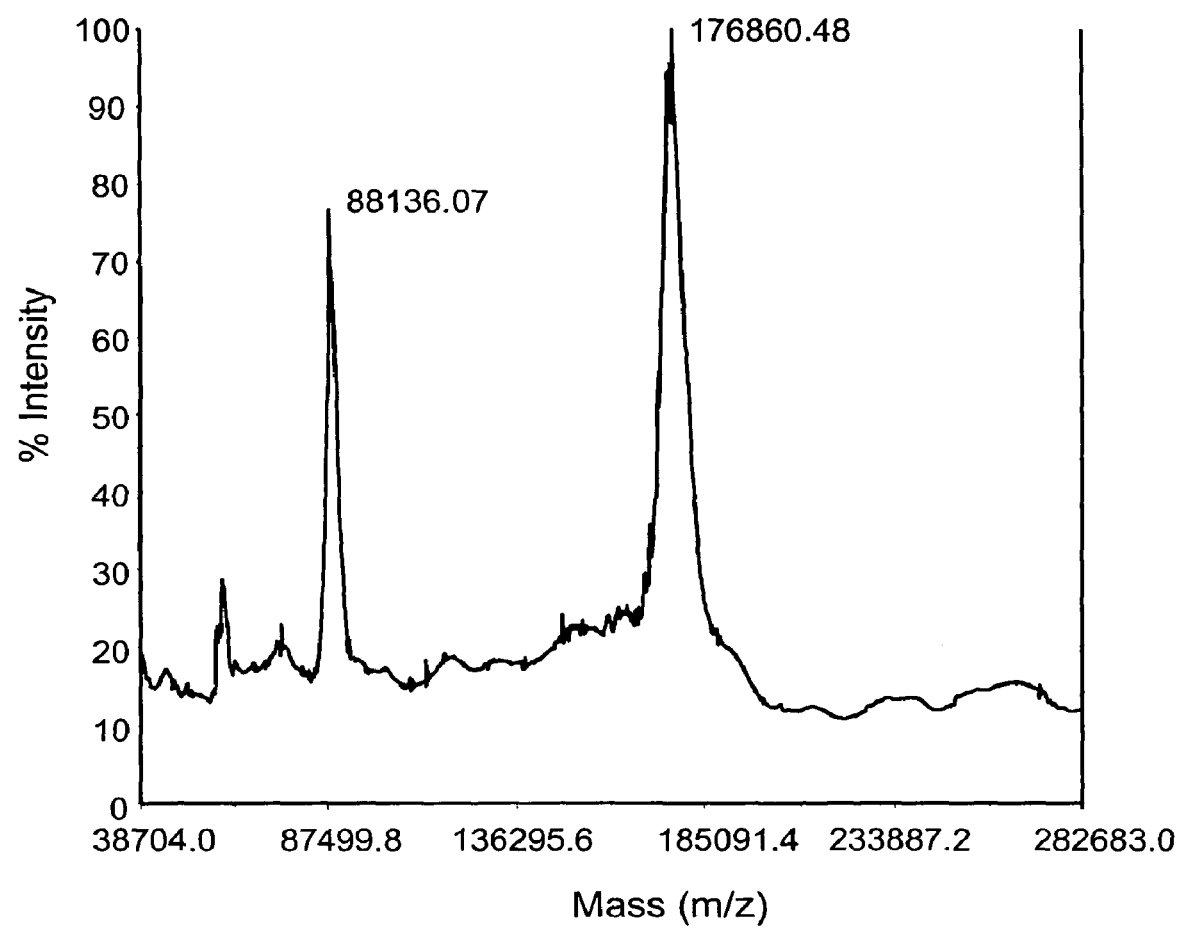
FIG. 6: a mass spectrum of hGH-PEG-IgG conjugates.

To determine the exact molecular weight of each protein conjugate, the purified samples were analyzed using MALDI-TOF (Voyager DE-STR, Applied Biosystems, USA) superspeed mass spectrometry. Sinapinic acid was employed as a matrix. 0.5 μl of each sample was spread on a slide glass and dried in the air. After an equal volume of the matrix was dropped on the slide glass, the slide glass was dried in the air and installed in an ion source. Detection was performed by a linear-mode TOF equipment using a positive method, and ions were accelerated by a total potential difference of about 2.5 kV in a divided extraction supply source using a delayed ion extractor at a delayed extraction time of 750 nsec/1500 nsec. The results of mass spectrometry analyses of hGH-PEG-IgG conjugate are shown in Table 1 and FIG. 6.

TABLE 1

Mass spectrometry analysis of IgG-protein conjugates

|  | Theoretical value (kDa) | Measured value (kDa) |
|---|---|---|
| HGH-PEG-IgG (Ex. 1) | 175.4 | 176.8 |
| IFN α-PEG-IgG (Ex. 3) | 172.6 | 172.6 |

TABLE 1-continued

Mass spectrometry analysis of IgG-protein conjugates

|  | Theoretical value (kDa) | Measured value (kDa) |
|---|---|---|
| G-CSF-PEG-IgG (Ex. 4) | 172.1 | 173.0 |
| $^{17}$S-G-CSF derivative-PEG-IgG (Ex. 4) | 171.9 | 172.2 |
| EPO-PEG-IgG (Ex. 5) | 185.4 | 183.0 |

The results showed that the purity of hGH-PEG-IgG conjugate was 90% or more, and that the measured molecular weight was nearly equal to the theoretical value. Further, the hGH-PEG-IgG conjugate was in the form of IgG bound to the hGH-PEG complex in a molar ratio of 1:1.

Figure 9:
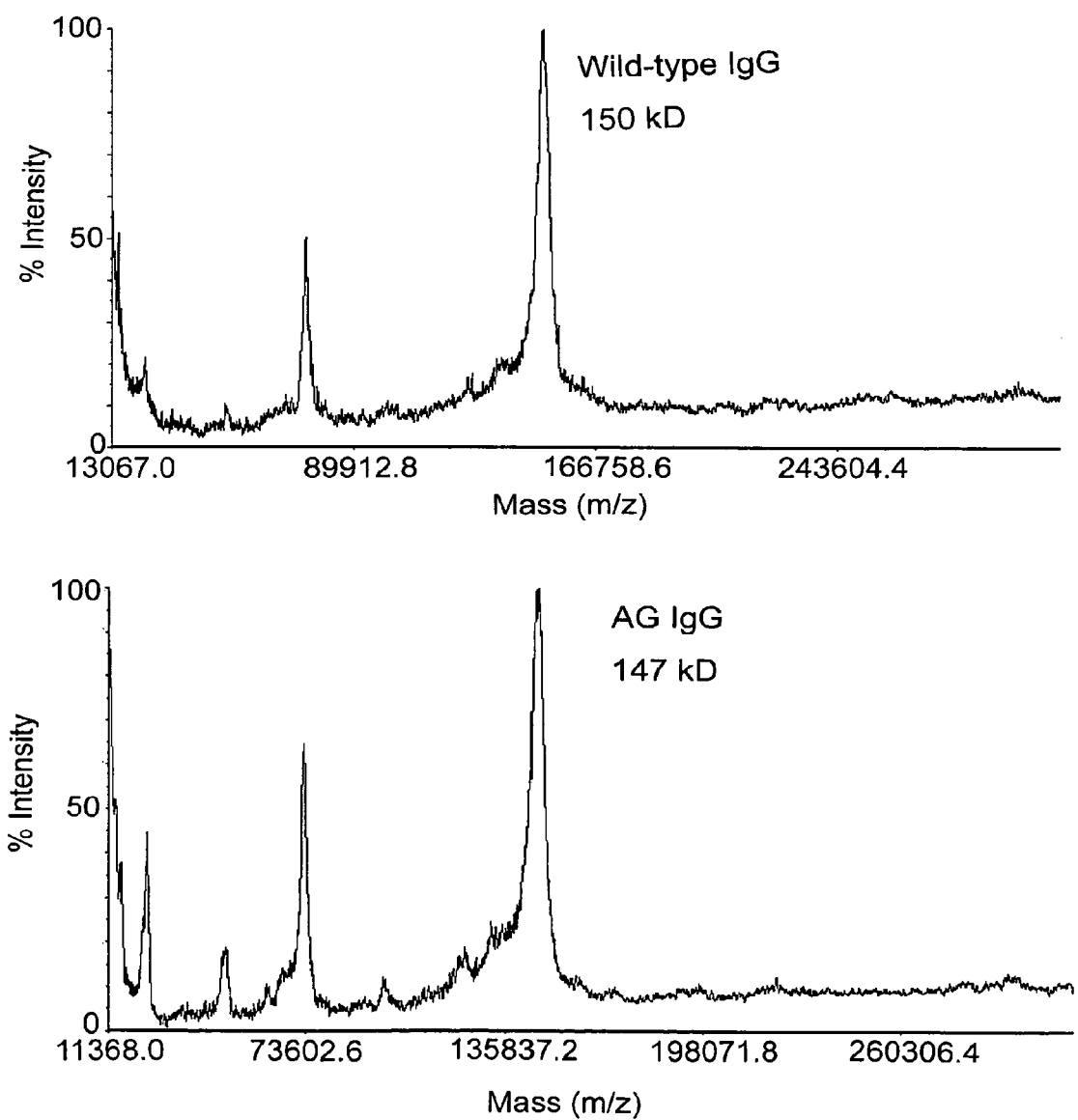
FIG. 9: a mass spectrum of aglycosylated IgG (AG IgG)

Further, the molecular weight of the AG IgG prepared in Example 10 as measured by the above MALDI-TOF method was 147 kDa, which was lower by 3,000 Da than the wild-type IgG (FIG. 9). This reduced molecular weight, 3,000 Da, corresponds to the theoretical size of sugar chain and, accordingly, it was concluded that the sugar chain of IgG was completely removed.

Table 2 shows the molecular weights of the IFN α-PEG-AG IgG and EPO-PEG-AG IgG conjugates prepared in Examples 11 and 12.

TABLE 2

Mass spectrometry analysis of AG IgG-protein conjugates

|  | Theoretical value (kDa) | Measured value (kDa) |
|---|---|---|
| IFN α-PEG-AG IgG (Ex. 11) | 169.6 | 170.0 |
| EPO-PEG-AG IgG (Ex. 12) | 182.4 | 180.0 |

TEST EXAMPLE 2

Pharmacokinetics Analysis I

In vivo stabilities and pharmacokinetic coefficients of the IgG-protein conjugates, PEG-protein and albumin-protein complexes (test group) prepared in Examples and Comparative Examples were compared with those of biologically active wild-type protein (control group). 5 Sprague-Dawley (SD) rats were used for each group in the following experiments. Mice received subcutaneous injections of 100 μg/kg of the control, PEG-complex, albumin-protein conjugate and IgG-protein conjugate, respectively. Blood samples were taken from the control group at 0.5, 1, 2, 4, 6, 12, 24, 30, 48, 72 and 96 hour after the injection, and the samples of the test groups, at 1, 6, 12, 24, 30, 48, 72, 96, 120, 240 and 320 hours after the injection. Blood samples were collected in a tube coated with heparin to prevent blood coagulation, and subjected to high-speed micro centrifugation at 4° C., 3,000×g for 30 min to remove cells. The protein concentration in sera was measured by ELISA method using the respective antibody specific for each biologically active protein.

Pharmacokinetic values of the wild-type hGH, IFN, G-CSF and EPO, and protein conjugates, complexes thereof are shown in Tables 2 to 6, in which $T_{max}$ means the time to reach the maximum drug concentration, $T_{1/2}$, half-life of a drug in blood, and MRT (mean residence time), average retention time in a body.

TABLE 3

Pharmacokinetic values of hGH

|  | Wild-type hGH | hGH-40K PEG (Comp. Ex. 1) | HGH-PEG-albumin (Comp. Ex. 2) | hGH-PEG-IgG (Ex. 1) |
|---|---|---|---|---|
| $T_{max}$ (hr) | 1.0 | 12 | 12 | 12 |
| $T_{1/2}$ (hr) | 1.1 | 7.7 | 5.9 | 13.9 |
| MRT (hr) | 2.1 | 18.2 | 13.0 | 19.0 |

TABLE 4

Pharmacokinetic values of IFN α

|  | Wild-type IFN α | IFN α-40K PEG (Comp. Ex. 1) | IFN α-PEG-albumin (Comp. Ex. 2) | IFN α-PEG-IgG (Ex. 3) | IFN α-PEG-AG IgG (Ex. 11) |
|---|---|---|---|---|---|
| $T_{max}$ (hr) | 1.0 | 30 | 12 | 30 | 24.0 |
| $T_{1/2}$ (hr) | 1.7 | 35.8 | 17.1 | 76.7 | 59.7 |
| MRT (hr) | 2.1 | 71.5 | 32.5 | 121.0 | 98.2 |

TABLE 5

Pharmacokinetic values of G-CSF

|  | Wild-type G-CSF | G-CSF-40K PEG (Comp. Ex. 1) | G-CSF-PEG-albumin (Comp. Ex. 2) | G-CSF-PEG-IgG (Ex. 4) |
|---|---|---|---|---|
| $T_{max}$ (hr) | 2.0 | 12 | 12 | 12 |
| $T_{1/2}$ (hr) | 2.8 | 4.8 | 5.2 | 8.4 |
| MRT (hr) | 5.2 | 24.5 | 25.0 | 35.7 |

TABLE 6

Pharmacokinetic values of $^{17}$S-G-CSF

|  | Wild-type $^{17}$S-G-CSF derivative | $^{17}$S-G-CSF derivative-40K PEG (Comp. Ex. 1) | $^{17}$S-G-CSF derivative-PEG-albumin (Comp. Ex. 2) | $^{17}$S-G-CSF derivative-PEG-IgG (Ex. 4) |
|---|---|---|---|---|
| $T_{max}$ (hr) | 2.0 | 24 | 24 | 48 |
| $T_{1/2}$ (hr) | 2.9 | 4.3 | 6.4 | 7.2 |
| MRT (hr) | 5.8 | 24.4 | 25.1 | 42.6 |

TABLE 7

Pharmacokinetic values of EPO

|  | Wild-type EPO | Highly glycosylated EPO (Darbepoetin-α) | EPO-PEG-IgG (Exp. 5) | EPO-PEG-AG IgG (Exp. 12) |
|---|---|---|---|---|
| $T_{max}$ (hr) | 6.0 | 12 | 48.0 | 48.0 |
| $T_{1/2}$ (hr) | 9.4 | 14.9 | 67.5 | 47.8 |
| MRT (hr) | 21.7 | 30.7 | 121.7 | 89.5 |

Figure 7:
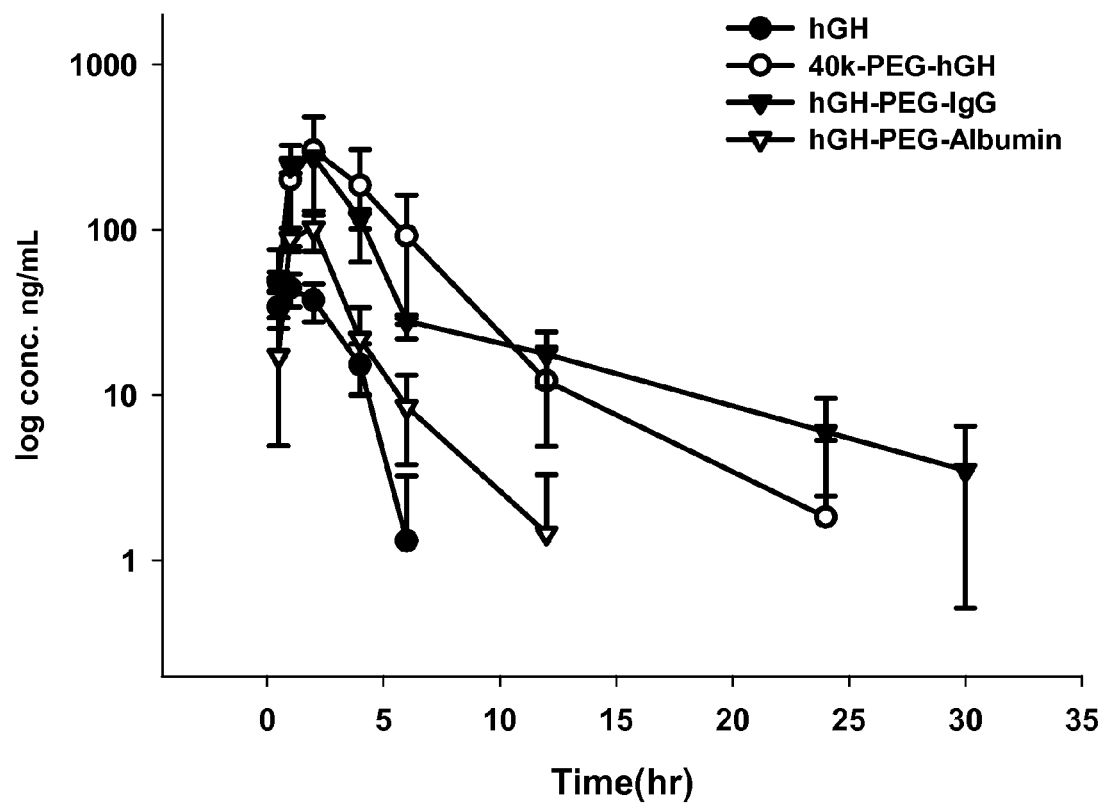
FIG. 7: a pharmacokinetic graph showing that hGH-PEG-IgG conjugates have serum stabilities superior to PEG-hGH complex.

As can be seen in Table 3 and FIG. 7, the half-life of the hGH-PEG-IgG conjugate was 13.9 hr, which is about 13-fold higher than that of wild-type hGH and about 2-fold higher than that of the hGH-40K PEG complex (7.7. hr) prepared in Comparative Example 1. The half-life of the hGH-PEG-albumin conjugate in which albumin is linked to the one end of PEG, not directly to hGH, was 5.9 hr. This result confirms that the inventive protein conjugate shows far superior durability in vivo.

Further, in Table 4 and FIG. 10, the results for IFN α were similar to those of hGH, but the effect of increasing the blood half-life observed in the inventive protein conjugate was far higher. While the half-life of wild-type IFN α was 1.7 hr, the half-life of 40 kDa PEG-IFN α complex increased to 35.8 hr and the half-life of IFN α-PEG-albumin conjugate, to 17.1 hr. As compared with these, the half-life of IFN α-PEG-IgG conjugate remarkably increased to 76.7 hr. Further, the half-life of IFN α-PEG-AG IgG conjugate was 59.7 hr which is nearly equal to that of IFN α-PEG-IgG conjugate. From this result, it can be seen that the absence of sugar chain does not effect on the in vivo stability of the conjugate.

As shown in Tables 5 and 6, the in vivo durability of G-CSF and its derivative showed a tendency similar to that of hGH and IFN. The half-life of 40 kDa PEG modified protein complexes and albumin conjugates were longer than those of wild-type G-CSF and its derivative. However, the inventive IgG protein conjugate showed a much longer half-life. Such an ability of the conjugated IgG to increase the drug stability in blood was also observed for amino acid modified derivatives. From these results, it can be anticipated that the inventive protein conjugate applied to other proteins would also exert the desired effect described above.

Figure 8:
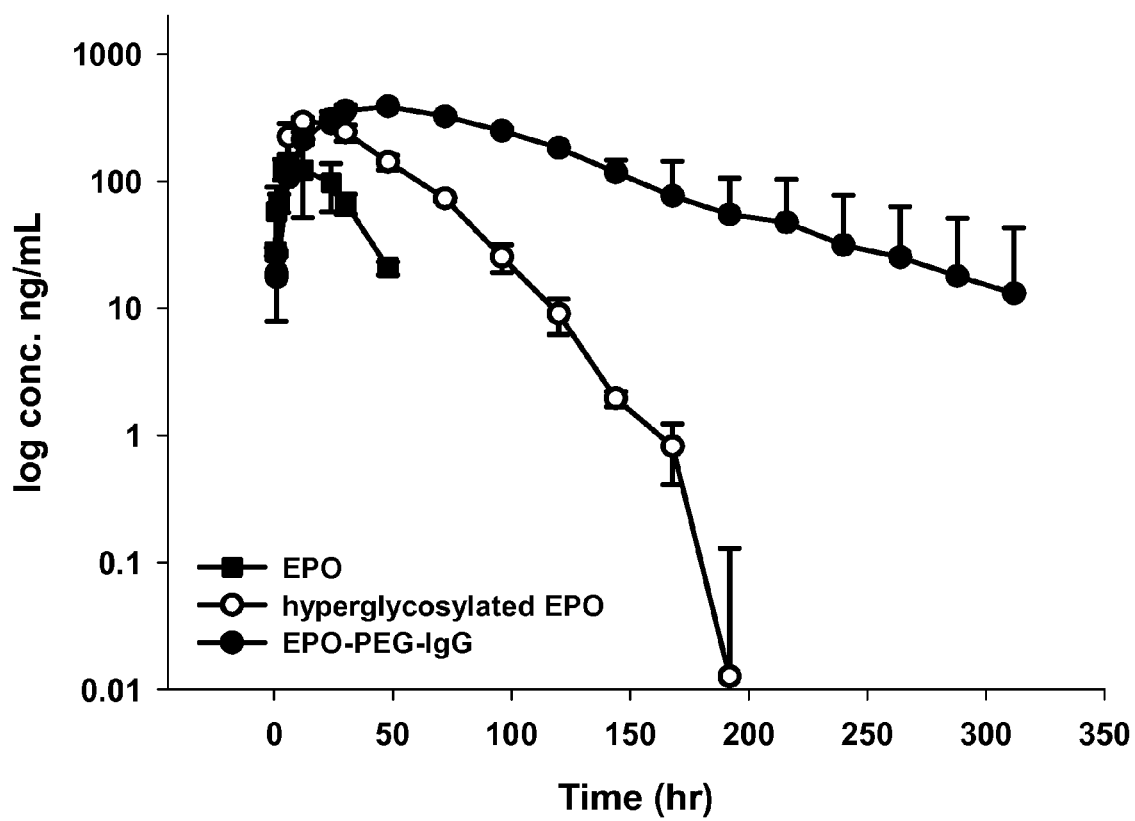
FIG. 8: a pharmacokinetic graph showing that erythropoietin-PEG-IgG conjugates have an enhanced circulating half-life as compared with the free erythropoietin or erythropoietin stabilized by hyper-glycosylation.

Table 7 and FIGS. 8 and 11 show that the effect of increasing the blood half-life of the inventive protein conjugate is evident for EPO having a glycosylated moiety. Namely, the blood half-life of wild-type EPO was 9.4 hr and that of highly glycosylated EPO having high blood stability, i.e, Darbepoetin-α (Aranesp, Amgen, USA), was 14.9 hr. In case of EPO-PEG-IgG conjugate, the blood half-life remarkably increased to 67.5 hr and that of the EPO-PEG-AG IgG conjugate also increased to 47.8 hr.

As can be seen from the above results, the inventive protein conjugates, wherein a physiological polypeptide is covalently bonded with a non-peptidic polymer and immunoglobulin, has an blood half-life which is dozen times higher than that of the wild-type protein. Further, the effect of increase of the blood half-life of the protein conjugate is still maintained at a similar level even if an aglycosylated immunoglobulin is employed.

Especially, as compared with 40 kDa PEG modified protein complex which has the highest blood durability among the previously reported PEG formulations, the inventive IgG protein conjugate exhibits far better durability. Further, relative to the protein conjugate coupled with albumin instead of IgG, the inventive protein conjugate showed markedly higher durability. These results suggest that the inventive protein conjugate can be effectively used for preparing a sustained formulation of a protein drug. The present findings, that the inventive protein conjugates exhibit markedly higher blood stability and longer MRT than previously reported PEG binding protein or albumin protein conjugate for a wide range of proteins including the G-CSF derivative having a point mutation, strongly suggests that such effect of increasing the blood stability and durability observed for the inventive protein conjugate would also be realized for any other biologically active peptides.

The half-life of hGH-PEG-IgG conjugate (Example 7) prepared using 10 kDa PEG as a non-peptide polymer was measured by the same method described above to be 9.5 hr, which is slightly shorter than that of hGH-PEG-IgG conjugate using 3.4 kDa PEG (13.9 hr). The apparent molecular weights and blood half-lives observed for those prepared using PEG having different functional groups, e.g., succinimidyl propionate, N-hydroxysuccinimidyl and butyl aldehyde groups, were similar to those prepared using PEG having aldehyde groups.

TEST EXAMPLE 3

Pharmacokinetics Analysis II

In order to measure the blood half-lives of Fab'-S-PEG-N-IgG and Fab'-N-PEG-N-IgG conjugates prepared in Examples 8 and 9, respectively, and Fab'-S-40K PEG complex prepared in Comparative Example 3, a pharmacokinetic analysis was carried out in accordance with the method of Test Example 2 by employing the conjugates, the complex and Fab' as a control. The result is shown in FIG. 12.

Figure 12:
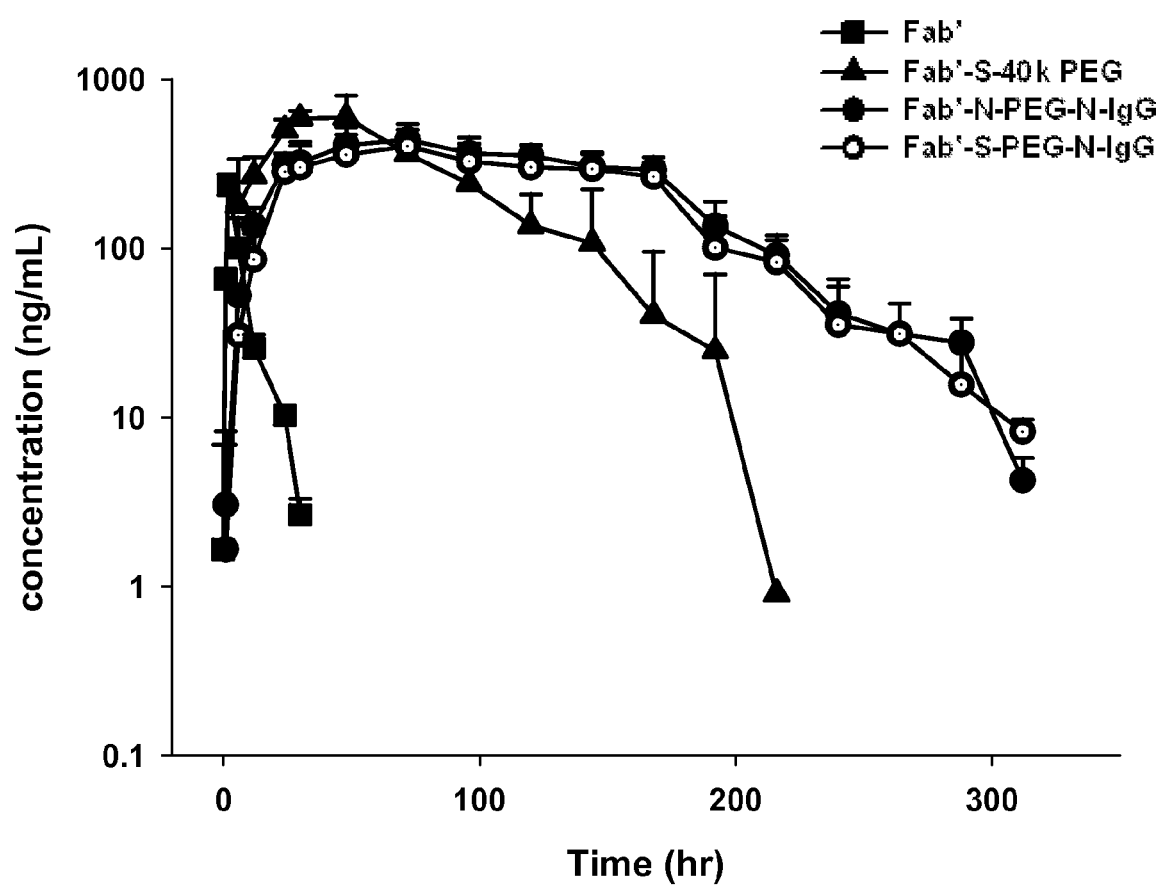
FIG. 12: a pharmacokinetic graph showing that Fab'-S-PEG-N-IgG and Fab'-N-PEG-N-IgG conjugates have an enhanced circulating half-life as compared with the wild-type Fab' and Fab'-S-40K PEG complex.

As can be seen in FIG. 12, Fab'-S-PEG-N-IgG and Fab'-N-PEG-N-IgG conjugates showed elongated blood half-lives which were two to three times longer than those of Fab' and Fab'-S-40K PEG complex.

TEST EXAMPLE 4

Measurement of in vitro Activity (1) Comparison of in vitro Activity of hGH Protein Conjugates In vitro activities of the hGH-PEG-IgG conjugate (Example 1), 40 kD PEG-hGH complex (Comparative Example 1) and hGH-PEG-albumin conjugate (Comparative Example 2) were measured by using rat node lymphoma cell line Nb2 (European Collection of Cell Cultures, ECCC #97041101) that undergo hGH dependent mitosis as follows.

Nb2 cells were cultivated in Fisher's medium supplemented with 10% fetal bovine serum (FBS), 0.075% $NaCO_3$, 0.05 mM 2-mercaptoethanol and 2 mM glutamine. The cells were incubated for additional 24 hours in the same medium without 10% FBS. After about $2 \times 10^4$ cells per well were added to a 96-well plate, various dilutions of hGH-PEG-IgG, 40 kDa PEG-hGH, hGH-PEG-albumin and a control (National Institute for Biological Standards and Control, NIBSC) were added to each well and the plates were incubated for 48 hours at 37° C. in a $CO_2$ incubator. To measure the extent of cell growth (the number of cells existed in each well), 25 µl of cell titer 96 Aqueous One Solution (Promega, USA) was added to each well and incubated for 4 hours at 37° C. Absorbance at 490 nm was measured to calculate the titer of each sample, and the calculated titers as shown in Table 8.

TABLE 8

In vitro activity analysis of hGH

| | Conc. (ng/ml) | Specific activity* (U/mg) | Relative activity to wild-type hGH (%) |
|---|---|---|---|
| Wild-type hGH | 100 | 2.71E+06 | 100 |
| Control (NIBSC) | 100 | 2.58E+06 | 95.2 |
| hGH-40K PEG | 100 | 0.206E+06 | 7.6 |
| hGH-PEG-albumin | 100 | 0.141E+06 | 5.2 |
| hGH-PEG-IgG | 100 | 0.86E+06 | 31.7 |

*Specific activity = $1/ED_{50} \times 10^6$ ($ED_{50}$: the amount of protein representing 50% of the maximum cell growth)

As can be seen from Table 8, all samples used in the experiments have in vitro activity. In addition, the in vitro activity of PEG modified hGH was lower than that of the unmodified hGH. In case of interferon, it was reported that 12 kDa PEG and 40 kDa PEG conjugates with IFNs showed activities which were only about 25% and 7% of the wild-type, respectively (P. Bailon et al., *Bioconjugate Chem.* 12:196-202, 2001). The larger the molecular weight of PEG increases, the lower the in vitro activity of PEG complex decreases. The in vitro activity of 40 kDa PEG modified hGH complex was only about 7.6% of wild-type hGH, and the hGH-PEG-albumin conjugate also showed a very low in vitro activity of about 5.2% of the wild-type. However, in case of conjugating IgG with the hGH-PEG complex, its relative activity was significantly enhanced to 30% or more of the wild-type. These results suggest that the inventive protein conjugates have both higher in vivo activity as well as prolonged blood half-life. In case of the IgG protein conjugates of the present invention, the increased protein activity is believed to be due to the increased blood stability caused by conjugation with IgG which plays the role of preserving the binding affinity to a receptor, and the non-peptidic polymer providing a spatial room. Such effect is expected to occur for IgG protein conjugates of any other biologically active proteins.

(2) Comparison of in vitro Activity of IFN α Protein Conjugates

To compare the in vitro activity of IFN α protein conjugates, anti-viral activity of IFN α-PEG-IgG complex (Example 3), 40 kDa PEG-IFN α conjugate (Comparative Example 1) and IFN α-PEG-albumin conjugate (Comparative Example 2) were measured by a cell culture biopsy method using Madin-Darby bovine kidney cells (MDBK cells; ATCC CCL-22) saturated with vesicular stomatitis virus (VSV). IFN α 2b having no PEG modification (NIBSC IFN) was employed as a control.

MDBK cells were cultured in MEM (minimum essential medium, JBI) supplemented with 10% FBS and 1% penicillin-streptomycin at 37° C. in a 5% $CO_2$ incubator. Samples and a control (NIBSC IFN) were diluted with the same culture medium to a constant concentration, and 100 µl of each dilution was added to 96-well plate. 100 µl of the cultured cell solution was added to each well, and the cells were incubated at 37° C. for about 1 hr in a 5% $CO_2$ incubator. After an hour, 50 µl of VSV having a viral concentration of $5-7 \times 10^3$ PFU was added to each well, and further incubated for 16 to 20 hours at 37° C. under 5% $CO_2$. Wells containing only cells and virus without samples or the control were employed as a negative control, and wells containing only cells without added viruses, as a positive control.

To remove the culture medium and to stain living cells, 100 µl of a neutral red solution was added to each well and further incubated at 37° C. for 2 hours in a 5% $CO_2$ incubator. After removing the supernatant by aspirating, the extraction solution (100 µl of a mixture of 100% ethanol and 1% acetate (1:1)) was added to each well. The stained cells were resuspended in the extraction solution with shaking and the absorbance at 540 nm was measured. $ED_{50}$ representing 50% of the maximum cell growth was calculated by regarding the cell growth of the positive control as 100% relative to the cell growth of the negative control.

TABLE 9

In vitro activity analysis of IFN α

| | Concentration (ng/ml) | $ED_{50}$ (IU/mg) | Relative activity to wild-type IFN (%) |
|---|---|---|---|
| Wild-type IFN α | 100 | 4.24E+08 | 100 |
| IFN α-40K PEG | 100 | 2.04E+07 | 4.8 |
| IFN α-PEG-albumin | 100 | 2.21E+07 | 5.2 |

TABLE 9-continued

In vitro activity analysis of IFN α

| | Concentration (ng/ml) | $ED_{50}$ (IU/mg) | Relative activity to wild-type IFN (%) |
|---|---|---|---|
| IFN α-PEG-IgG | 100 | 4.75E+07 | 11.2 |
| IFN α-PEG-AG IgG | 100 | 4.32E+07 | 10.2 |

As shown in Table 9, the activity of PEG modified IFN α was lower than that of unmodified IFN α. Especially, the blood stability increased as the molecular weight of PEG moiety increased, but the relative activity gradually decreased. A 40 kDa PEG modified IFN α complex showed a very low in vitro activity corresponding to about 4.8% of the wild-type activity. As mentioned above, there was a previous report that 12 kDa PEG and 40 kDa PEG conjugated IFNs showed about 25% and 7% in vitro activity of the wild-type, respectively (P. Bailon et al., *Bioconjugate Chem.* 12:196-202, 2001). Namely, since if the molecular weight of PEG increases, the blood half-life increases but its pharmaceutical effect suddenly decreases, there has been a need to develop a substance having improved pharmaceutical activity and prolonged half-life. The IFN α-PEG-albumin conjugate also showed a very low in vitro activity corresponding to only about 5.2% of the wild-type. However, in case of modifying IFN α with IgG (IFN α-PEG-IgG conjugate), the relative activity increased to 11.2% of the wild-type. Further, IFN α-PEG-AG IgG conjugate showed in vitro activity corresponding to 10.2% of the wild-type and, accordingly, it was concluded that the absence of sugar chain has no significant effect on the activity of a protein conjugate.

These results show that the inventive IgG protein conjugate exhibits high in vivo activity together with prolonged half-life.

(3) Comparison of in vitro Activity of G-CSF Protein Conjugates

The in vitro activities of wild-type G-CSF (Filgrastim), $^{17}$Ser-G-CSF derivative, 20 kDa PEG-G-CSF complex (Neulasta, USA), 40 kDa PEG-$^{17}$S-G-CSF derivative complex, $^{17}$Ser-G-CSF derivative-PEG-albumin conjugate and $^{17}$S-G-CSF derivative-PEG-IgG conjugate were measured.

First, human myelogenous originated cells, HL-60 (ATCC CCL-240, Promyelocytic leukemia patient/36 yr old Caucasian female) cells, were cultivated in RPMI 1640 medium supplemented with 10% FBS, and the number of cells were adjusted to about $2.2 \times 10^5$ cells/ml. DMSO (dimethylsulfoxide, culture grade/SIGMA) was added to the cells to a concentration of 1.25% (v/v). 90 μl of the DMSO treated culture solution having about $2 \times 10^4$ suspended cells per well was added to 96-well plate (Corning/low evaporation 96 well plate) and incubated at 37° C. for 72 hours in a 5% $CO_2$ incubator.

The concentration of each sample was determined by using a G-CSF ELISA kit (R & D Systems, USA), and each sample was diluted with RPMI 1640 medium at a proper ratio to a concentration of 10 μg/ml. The resulting solution was subjected to 19 cycles of sequential half dilution with RPMI 1640 medium.

10 μl of each sample prepared above was added to each well having HL-60 cells on cultivation, and the concentration was reduced by half from 1,000 ng/ml. The microplates treated with protein samples were further incubated at 37° C. for 72 hour.

To examine the extent of cell growth after the incubation, the number of cells were determined by measuring absorbance at 670 nm using CellTiter96® (Promega, USA).

TABLE 10

In vitro activity analysis of G-CSF derivative

| | $ED_{50}$ (IU/ml) | Relative activity to wild-type G-CSF (%) |
|---|---|---|
| Wild-type G-CSF (Filgrastim) | 0.30 | 100 |
| $^{17}$Ser-G-CSF derivative | 0.26 | 115 |
| 20K PEG-G-CSF (Neulasta) | 1.20 | 25 |
| $^{17}$Ser-G-CSF derivative-40K PEG | 10.0 | <10.0 |
| $^{17}$Ser-G-CSF derivative-PEG-albumin | 1.30 | 23.0 |
| $^{17}$Ser-G-CSF derivative-PEG-IgG | 0.43 | 69.0 |

As can be seen from Table 10, the IgG protein conjugate of $^{17}$Ser-G-CSF derivative having an amino acid modification showed an effect similar to that observed for the protein conjugate of the wild-type. It has been already confirmed that the $^{17}$Ser-G-CSF derivative modified with PEG shows a longer half-life but a lower activity than the unmodified (Korean Patent Application No. 2003-17867). Specially, while the blood stability of PEG modified $^{17}$Ser-G-CSF derivative increased as the molecular weight of the PEG moiety increased, its relative activity gradually decreased. 40 kDa PEG modified $^{17}$Ser-G-CSF derivative complex showed a very low in vitro activity corresponding to about 10% of the wild-type. Namely, as the molecular weight of PEG increases, the blood half-life increases but its pharmaceutical effect suddenly decreases, there has been a need to develop a substance having improved pharmaceutical activity and prolonged half-life. Meanwhile, the $^{17}$Ser-G-CSF derivative modified with albumin showed a relatively low in vitro activity corresponding to only about 23% of the wild-type. However, in case of modifying $^{17}$Ser-G-CSF derivative with IgG ($^{17}$Ser-G-CSF-PEG-IgG conjugate), its relative activity increased in a level which is 69% or more of the wild-type. These results show that the inventive IgG protein conjugate exhibits high in vivo activity together with prolonged half-life.

(4) Comparison of in vitro Activity of EPO Protein Conjugates

The in vitro activities of wild-type EPO (BRP, UK), highly glycosylated EPO (Aranesp, USA) and EPO-PEG-IgG conjugate were measured.

First, human bone marrow originated cells, TF-1 cells (ATCC CRL-2003, erythroleukemia), were cultivated in RPMI 1640 medium supplemented with 10% FBS and 12 ng/ml of GM-CSF, and then, in the same RPMI 1640 medium lacking GM-CSF for one day. 50 μl of the culture solution having about $2 \times 10^4$ cells was added to each well of a 96-well plate (Corning/low evaporation 96 well plate) and incubated at 37° C. for 72 hours in a 5% $CO_2$ incubator.

The concentration of each sample was determined by using an EPO ELISA kit (R & D Systems, USA), and each sample was diluted with RPMI 1640 medium at a proper ratio to a concentration of 10 μg/ml. The resulting solution was subjected to 19 cycles of serial two-fold dilution with RPMI 1640 medium.

50 μl of each sample prepared above was added to each well having TF-1 cells on cultivation, and the concentration was reduced by half from 5 μg/ml. The microplates treated with protein samples were further incubated at 37° C. under 5% $CO_2$ for 72 hour.

To examine the extent of cell growth after the incubation, the number of cells were determined by measuring the absorbance at 490 nm using CellTiter96® AQueous One (Cat. No. G3581, Promega, USA).

TABLE 11

In vitro activity analysis of EPO

| | Specific activity (U/mg) | Relative activity to wild-type EPO (%) |
|---|---|---|
| Wild-type EPO (BRP) | $8.9 \times 10^5$ | 100 |
| Highly glycosylated EPO(Aranesp) | $6.8 \times 10^4$ | 7.6 |
| EPO-PEG-IgG | $3.7 \times 10^4$ | 4.2 |

As can be seen from Table 11, all samples used in the experiments have in vitro activity as approved by their promotion of the growth of the human bone marrow originated cells. In addition, the in vitro activities of the highly glycosylated EPO and PEG-IgG complex-modified EPO were lower than that of the unmodified EPO. However, the inventive EPO protein conjugate is expected to have an in vivo activity superior to the unmodified EPO due to its significantly prolonged blood half-life. In case of the EPO protein conjugates of the present invention, the increased protein activity is believed to be due to the increased blood stability caused by conjugation with IgG which plays the role of preserving the binding affinity to a receptor, and the non-peptidic polymer providing a spatial room.

(5) Neutralization of Cytotoxicity by Fab' Protein Conjugates

In vitro activities of Fab'-S-PEG-N-IgG and Fab'-N-PEG-N-IgG conjugates prepared in Examples 8 and 9, respectively, and Fab'-S-40K PEG complex prepared in Comparative Example 3 were examined by measuring their ability for neutralizing the cytotoxicity of TNF-α on mouse fibroblast cell line L929 (ATCC CRL-2148), as follows.

Each of the Fab' conjugates and the complex was subjected to serial two-fold dilutions and each of 100 μl aliquots of the dilutions was added to a well of a 96-well plate. RhTNF-α (R&D systems) and actinomycin D (sigma), an inhibitor of RNA synthesis, were added to the wells to concentrations of 10 ng/ml and 1 μg/ml, respectively. Then the mixture was reacted at 37° C., 5% $CO_2$ for 30 minutes, and transferred to an analyzing microplate. 50 μl each of L929 cell line culture was added to each well to a concentration of $5 \times 10^4$ cells/well. The cells were incubated at 37° C. under 5% $CO_2$ for 24 hours. The culture solution in the well was removed and 50 μl each of 5 mg/ml MTT (sigma) in PBS was added to each well. The cells were incubated at 37° C., 5% $CO_2$ for 4 hours. 150 μl of DMSO was added to each well and dissolved. The absorbance at 540 nm was measured to determine the extent of neutralization of the cytotoxicity of rhTNF-α by the test Fab' conjugates and complex. Purified Fab' obtained in step 1 of Example 8 was employed as a control.

Figure 13:
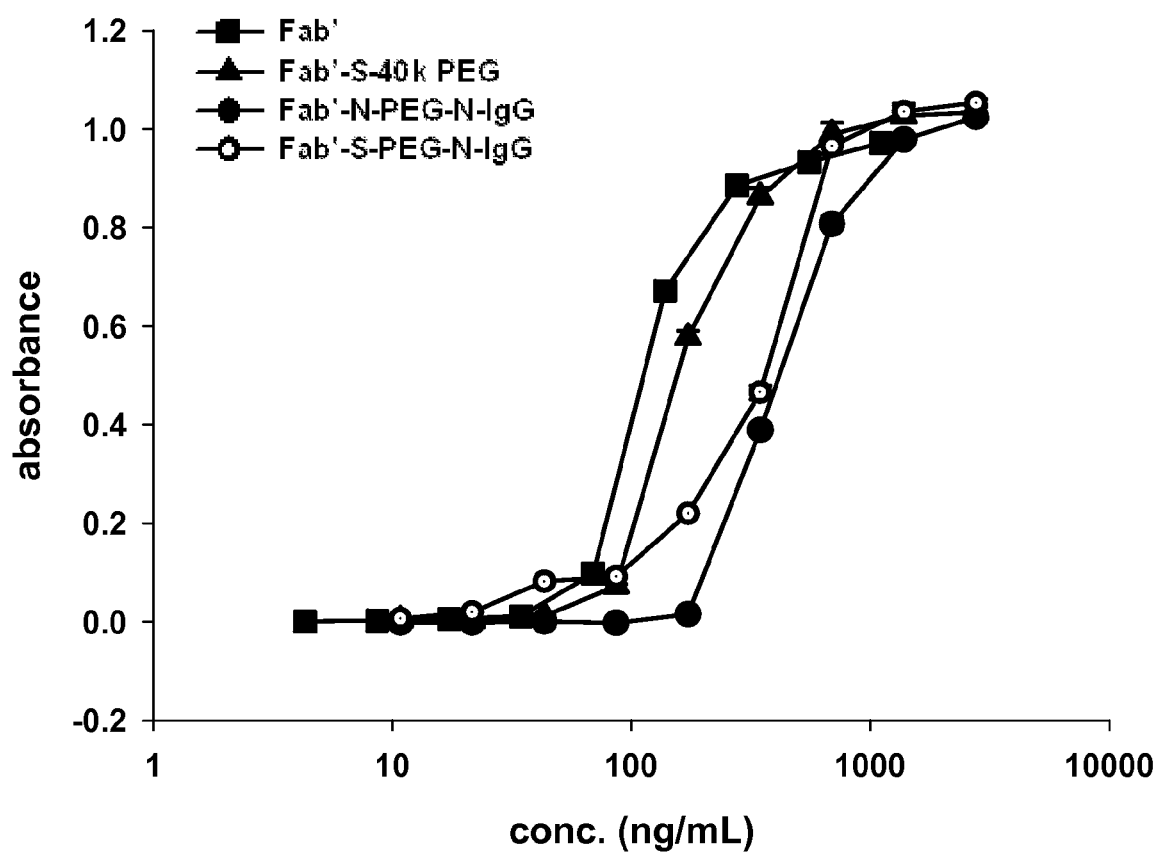
FIG. 13: a graph showing in vivo activities of Fab', Fab'-S-40K PEG complex, Fab'-S-PEG-N-IgG conjugate and Fab'-N-PEG-N-IgG conjugate.

As can be seen from the result in FIG. 13, all of the protein conjugates and complex showed absorbances similar to that of Fab'. This result show that Fab'-PEG-IgG conjugates, wherein an immunoglobulin is linked to the N-terminal or to the free —SH group adjacent to the C-terminal of Fab' through a PEG spacer, maintains the biological activity of Fab'.

TEST EXAMPLE 5

Measurement of in vivo Activity in Animal Model (1) Comparison of in vivo Activity of hGH Protein Conjugates 10 hypsectomized male Sprague Dawley rats (5-week old, SLC, USA) were employed for each group in a body weight gaining test to measure the in vivo activities of hGH-PEG-IgG conjugate, hGH-40K PEG complex and wild-type hGH. A solvent control, wild-type hGH, hGH-PEG-IgG conjugate and hGH-40K PEG complex were subcutaneously injected into the rat's back of the shoulder using a 26G syringe (1 ml, Korea Vaccine Co., Ltd.) according to the administration schedule and dose described in Table 12. Rats' weights were measured before the injection and 16 hours after the injection. Rats were sacrificed with ether 24 hours after the final injection, and the presence of pituitary gland was examined with the naked eye to exclude the rats having observable residual pituitary gland from the result.

TABLE 12

Condition for in vivo activity test of hGH in animal models

| Group | Drug | Average daily dose (day) | Total amount of administration | Administration schedule |
|---|---|---|---|---|
| 1 | Solvent control | — | PBS (0.5 ml) | Once/day, Daily administration for 12 days |
| 2 | Wild-type hGH | 30 μg | 360 mIU (30 μg/time) | Once/day, Daily administration for 12 days |
| 3 | hGH-40K PEG | 30 μg | 360 mIU (180 μg/time) | Once/6 days, Twice administration |
| 4 | hGH-PEG-IgG | 30 μg | 360 mIU (180 μg/time) | Once/6 days, Twice administration |
| 5 | hGH-PEG-IgG | 10 μg | 120 mIU (60 μg/time) | Once/6 days, Twice administration |

Figure 14:
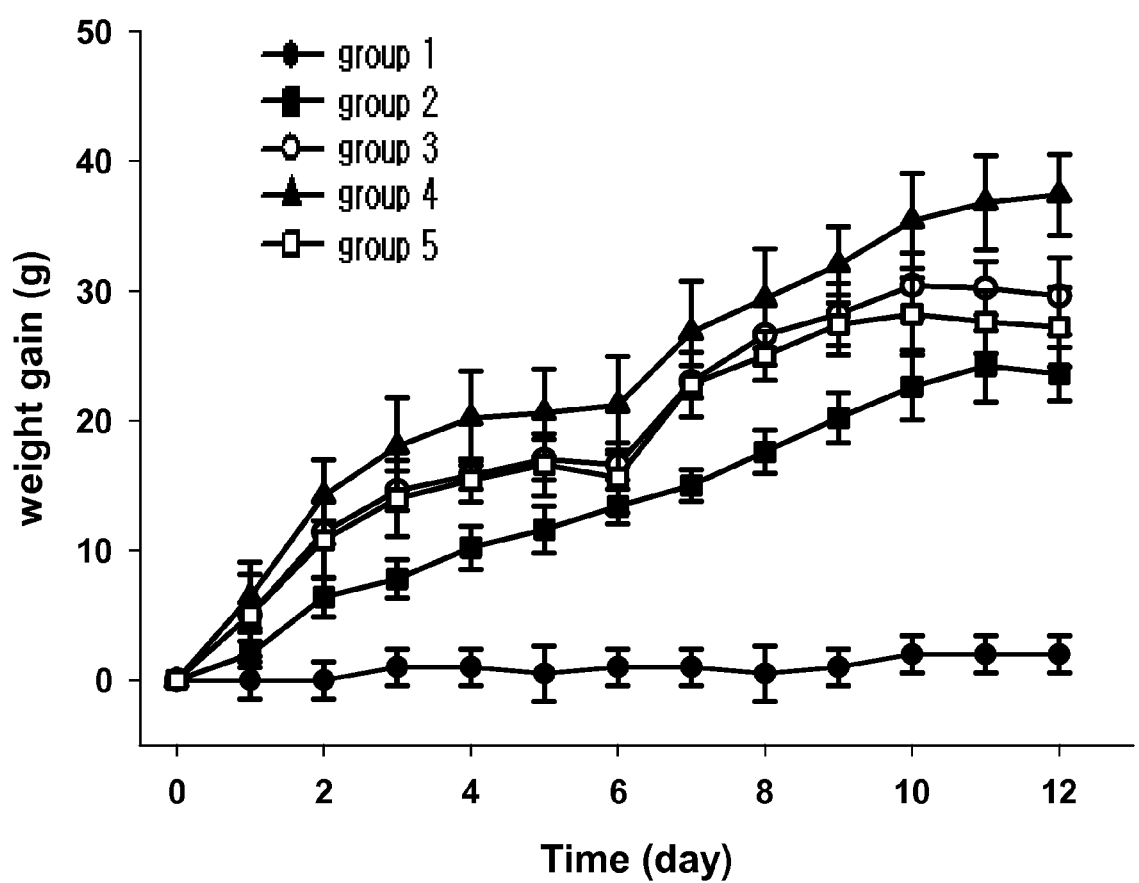
FIG. 14: In vivo activity of hGH-PEG-IgG conjugates based on the time-dependent weight change of rats after the injection of vehicle only (30 μg/day; group 1), wild-type hGH (30 μg/day; group 2), hGH-PEG (30 μg/day; group 3), hGH-PEG-IgG conjugate (30 μg/day; group 4), and hGH-PEG-IgG conjugate (10 μg/day; group 5)

The change in the weight after the administration of each sample was showed in FIG. 14. Since the wild-type hGH used as a standard (control) must be administered everyday to maintain its in vivo activity, it was administered once a day for 12 days, and accordingly, rats of Group 2 gained weight during the administration. In rats of Group 3 administered with the hGH-40 kDa PEG complex once/6 days, gained weight continuously till 3 days after the administration, and the rate of increase slowed down thereafter. These results coincided with the expectation based on the results of Test Examples 1 and 2 that the hGH-PEG complex showed far longer half-life and higher in vivo activity than the wild-type hGH. Especially, the effect generated by administering hGH-PEG-IgG conjugate once/6 days in an amount corresponding to a third of the wild-type dose was equal or better than daily administration of the wild-type. This means that the in vivo activity of hGH-PEG-IgG conjugate is more than 3-fold higher than that of the wild-type.

(2) Comparison of in vivo Activity of G-CSF Derivative Protein Conjugates

In order to examine the effect of the inventive protein conjugates with [17]Ser-G-CSF having a substitution of $17^{th}$ amino acid by serine, the in vivo activities of wild-type G-CSF, a commercially available 20 kDa PEG-G-CSF complex and [17]Ser-G-CSF-PEG-IgG conjugate were compared. The [17]Ser-G-CSF-PEG-IgG conjugate of the present invention was dissolved in a solvent comprising 20 mM sodium phosphate, 1% glycine and 0.25% mannitol (pH 7.0). Wild-type methionyl G-CSF complex (Filgrastim, Amgen, USA) and 20 kDa PEG modified G-CSF (Neulasta, Amgen, USA) dissolved in the same solvent were employed as a comparative group. Male 7-week-old ICR mice were purchased from Samtaco Bio (Korea) and subjected to an acclimation period for a week before the experiment. At the beginning of the experiment, the weight of ICR mice were in the range of 30-35 g. They were allowed to freely ingest formula feed (Samyang Corporation, Korea) and water during the acclimation and experiment, and kept in a cage under the condition of 22±3° C., 55±5% of relative humidity, 10-12 times/hr ventilation, 150-200 lux of illumination intensity and a daily lightening cycle of 12 hrs light/12 hrs dark. Each experimental group consisted of 5 mice, and a complex anticancer agent and each sample were administered to the mice according to the administration schedule and dose described in Table 13. Neutropenia animal model was prepared by injecting once a mixture of 130 mg/kg of cyclohexamide (CPA; Sigma, USA), 4.5 mg/kg of doxorubicin (DXR; Sigma, USA) and 1 mg/kg of vincristin (VCR, Sigma, USA) into the abdominal cavity of ICR mice. No treatment group did not receive the anticancer agent administration and show no reduction of neutrophil. The solvent control is the group which was administered with anticancer agent to reduce the number of neutrophil and with adjuvant only instead of a drug sample. The wild-type G-CSF was subcutaneously injected at a dose of 100 µg/kg/day around 10 a.m. everyday from the first day till the fifth day after the anticancer agent administration. The $^{17}$S-G-CSF-IgG and 20 kDa PEG-G-CSF complexes (Neulasta, Amgen, USA) were injected once at the first day after the anticancer agent administration, at a dose of 1,000 µg/kg that corresponds to a dose for five days when a two-fold amount of the wild-type dose was regarded as a daily dose (200 µg/kg/day). 0.3-0.5 ml of blood was taken from mice's orbital vein at day 1, 2, 3, 4, 5, 6 and 8 after the anticancer agent administration. Blood collection was performed around 4 p.m., 6 hours after the injection of a drug sample. The numbers of white blood cells (WBC), red blood cells (RBC) and platelet were measured using an automatic hematocyte counter. In addition, a blood spread specimen was prepared and subjected to Giemsa staining. Each hematocyte was differentially calculated to obtain the ratio of neutrophil, and then, the number of neutrophil was calculated by formula I based on the ratio of neutrophil.

Number of neutrophil (cells/mm$^3$)=total number of WBC (cells/mm$^3$)×the ratio of neutrophil (%)×1/100      Formula 1

To examine the statistical significance of the values observed for the no treatment group, solvent control group and $^{17}$S-G-CSF derivative PEG-IgG group, statistical analysis was performed about the number of hematocyte and weight of each group using Student's t-test.

TABLE 13

Condition for testing the activity of a protein increasing the number of neutrophils in an animal model

| Group | Drug | Average daily dose (kg/day) | Total amount of administration | Administration schedule |
|---|---|---|---|---|
| 1 | No treatment | — | PBS (0.5 ml) | Once/day, Daily administration for 5 days |
| 2 | Solvent control | — | PBS (0.5 ml) | Once/day, Daily administration for 5 days |
| 3 | Wild-type G-CSF (Filgrastim) | 100 µg | 500 µg/kg/ 5 times | Once/day, Daily administration for 5 days |
| 4 | 20K PEG-G-CSF (Neulasta) | 200 µg | 1,000 µg/kg/ time | Once administration |
| 5 | $^{17}$S-G-CSF derivative PEG-IgG | 200 µg | 1,000 µg/kg/ time | Once administration |

The recovery of neutrophil after the administration of each sample is shown in FIG. 15. When the wild-type G-CSF used as a standard was injected everyday for 5 days, the number of neutrophil gradually increased during the administration and finally reached a maximum at day 5. While the 20 kDa PEG-G-CSF complex administered once at twofold amount of the daily dose showed only two-thirds of the in vivo activity observed for the daily administration of wild-type G-CSF, the $^{17}$S-G-CSF derivative-PEG-IgG conjugate exhibited an activity which was 3-fold higher than the in vivo activity of 20 kDa PEG-G-CSF complex. Further, the inventive protein conjugate generated two-fold higher effect for recovering neutrophil than daily administration of G-CSF, which coincided with the expectation based on the result that the $^{17}$S-G-CSF derivative-PEG-IgG conjugate had significantly longer blood half-life and higher in vivo activity than the wild-type. These results show that the same effect of the inventive protein conjugate caused by covalently binding IgG to PEG can be expected of a protein derivative having an amino acid modification as well as the wild-type. Accordingly, the protein conjugate of the present invention can be effectively employed as a long-acting formulation satisfying the goals of significantly increasing the blood half-life and in vivo activity of G-CSF while overcoming the problem of the wild-type G-CSF requiring too frequent administrations.

(3) Comparison of in vivo Activity of EPO Protein Conjugate

In order to compare the in vivo activities of wild-type EPO, a highly glycosylated EPO (Aranesp, USA) and an EPO-PEG-IgG conjugate, changes in the blood components of the rats administered with the above test samples were examined. The experiment was carried out as follows, with a slight modification of the method described by J. C. Egrie and Browne (*British Journal of Cancer* (2001) B4 (Supplement 1), 3-10).

The EPO-PEG-IgG conjugate of the present invention was dissolved in a solvent comprising 20 mM sodium phosphate, 1% glycine and 0.25% mannitol (pH 7.0). Wild-type EPO and the highly glycosylated EPO dissolved in the same solvent were employed as comparative groups. Male 7-week-old rats were purchased from Daehan Biolink Inc. (Korea) and subjected to an acclimation for a week before the experiment. At the beginning of the experiment, the weight of ICR mice were in the range of 200-250 g. They were allowed to freely ingest formula feed (Cheiljedang Co., Korea) and water during the acclimation and experiment, and kept in a cage under the condition of 22±3° C., 55±5% relative humidity, 10-12 times/hr ventilation, 150-200 lux illumination intensity and a daily lightening cycle of 12 hrs light/12 hrs dark. Each experimental group consisted of 5 rats, and each test sample prepared as above was subcutaneously injected into the rat's back of the shoulder using a 26G syringe (1 ml, Korea Vaccine Co., Ltd.) according to the administration schedule and dose described in Table 14.

After the administration, whole blood samples were taken from the tail vein of the rats into a tube containing anti-clotting agent (EDTA), every 3 days for one month. Hematocrit of the blood samples was measured with an automatic hematocyte counter (Vet ABC).

TABLE 14

Condition for testing the activity of a protein increasing hematocrit in animal models

| Group | Drug | Total amount of administration | Administration schedule |
|---|---|---|---|
| 1 | Solvent control | PBS (0.5 ml) | Once administration |
| 2 | Wild-type EPO | 8 µg/kg/5 times | Once/day, Daily administration for 5 days |
| 3 | Highly glycosylated EPO (Anaesp) | 8 µg/kg/time | Once administration |
| 4 | EPO-PEG-IgG | 8 µg/kg/time | Once administration |

The recovery of hematocrit after the administration of each sample is shown in FIG. 16. When the wild-type EPO used as a standard was injected everyday for 5 days, the hematocrit gradually increased during the administration and finally reached a maximum at day 9. In the rats of group 3 administered with the highly glycosylated EPO, hematocrit increased fast for 6 days after the injection, then decreased rapidly thereafter. In contrast, the inventive EPO-PEG-IgG conjugate exhibited a higher and faster rate of initial increase of hematocrit than the highly glycosylated EPO, and maintained a higher in vivo activity than the other test proteins for more than two weeks. These results coincided with the expectation based on the results of Test Example 2 that the EPO-PEG-IgG conjugate showed a far longer blood half-life than the wild-type EPO and the highly glycosylated EPO. Accordingly, the protein conjugate of the present invention can be effectively employed as a long-acting formulation satisfying the goals of significantly increasing the blood half-life and in vivo activity of EPO while overcoming the problem of the wild-type EPO, which requires too frequent administration.

What is claimed is:

1. A protein conjugate of (A) a physiologically active polypeptide, (B) a non-peptidic polymer, and (C) immunoglobulin G,
    wherein the physiologically active polypeptide (A) is selected from the group consisting of human growth hormone, interferon alpha, interferon beta, granulocyte colony stimulating factor, and erythropoietin,
    wherein the non-peptidic polymer (B) is poly(ethylene glycol),
    wherein the physiologically active polypeptide (A) and the immunoglobulin G (C) are covalently linked through the non-peptidic polymer (B); and
    wherein the conjugate shows a prolonged in vivo half-life of the physiologically active polypeptide (A).

2. The protein conjugate according to claim 1, wherein the non-peptidic polymer (B) has reactive groups at both ends, the reactive group at one end being covalently linked to the physiologically active polypeptide (A) and the reactive group at the other end being covalently linked to the immunoglobulin G (C).

3. The protein conjugate according to claim 2, wherein the reactive group of the non-peptidic polymer (B) is selected from the group consisting of aldehyde, propion aldehyde, butyl aldehyde, maleimide and succinimide derivative.

4. The protein conjugate according to claim 3, wherein the succinimide derivative is succinimidyl propionate, succinimidyl carboxymethyl, hydroxy succinimidyl or succinimidyl carbonate.

5. The protein conjugate according to claim 3, wherein the non-peptidic polymer (B) has aldehyde groups at both ends.

6. The protein conjugate according to claim 1, wherein the immunoglobulin G (C) is selected from the group consisting of IgG1, IgG2, IgG3, and IgG4.

7. The protein conjugate according to claim 1, wherein the immunoglobulin G (C) is a human immunoglobulin.

8. The protein conjugate according to claim 1, wherein the immunoglobulin G (C) is selected from the group consisting of an immunoglobulin having an increased or decreased degree of glycosylation, and an aglycosylated immunoglobulin.

9. The protein conjugate according to claim 8, wherein the increase or decrease of the degree of glycosylation or aglycosylation of an immunoglobulin is conducted by a method selected from the group consisting of a chemical method, enzymatic method, biotechnological method and a combination thereof.

10. The protein conjugate according to claim 1, wherein the non-peptidic polymer (B) is covalently linked at the ends thereof to the amino terminal, lysine residue, histidine residue or cysteine residue of the immunoglobulin and the amino terminal, lysine residue, histidine residue or cysteine residue of the physiologically active polypeptide, respectively.

11. A method for preparing the protein conjugate of claim 1, comprising:
    (a) covalently linking a physiologically active polypeptide and immunoglobulin G with a non-peptidic polymer, said non-peptidic polymer having reactive groups at both ends; and
    (b) isolating a protein conjugate of the active polypeptide, the immunoglobulin and the non-peptidic polymer, wherein the physiologically active polypeptide and the immunoglobulin are covalently linked through the non-peptidic polymer,
    wherein the physiologically active polypeptide is selected from the group consisting of human growth hormone, interferon alpha, interferon beta, granulocyte colony stimulating factor, and erythropoietin; and
    wherein the non-peptidic polymer is a poly(ethylene glycol).

12. The method according to claim 11, wherein step (a) comprises:
    (a1) covalently coupling one end of the non-peptidic polymer with either the immunoglobulin or the physiologically active polypeptide;
    (a2) isolating from the resulting reaction mixture a complex comprising the non-peptidic polymer coupled with the immunoglobulin or the physiologically active polypeptide; and
    (a3) covalently coupling the free end of the non-peptidic polymer of the complex with the immunoglobulin or physiologically active polypeptide, to produce a protein conjugate comprising the physiologically active polypeptide, the non-peptidic polymer and the immunoglobulin, which are covalently interlinked.

13. The method according to claim 12, wherein the molar ratio of the physiologically active polypeptide to the non-peptidic polymer in step (a1) ranges from 1:2.5 to 1: 5.

14. The method according to claim 12, wherein the molar ratio of the immunoglobulin to the non-peptidic polymer in step (a1) ranges from 1:5 to 1:10.

15. The method according to claim 12, wherein steps (a1) and (a3) are performed in the presence of a reducing agent.

16. The method according to claim 15, wherein the reducing agent is sodium cyanoborohydride, sodium borohydride, dimethylamine borate or pyridine borate.

17. The protein conjugate according to claim 1, wherein the immunoglobulin G has the wild-type glycosylation.

* * * * *